US006207419B1

(12) United States Patent
Church et al.

(10) Patent No.: US 6,207,419 B1
(45) Date of Patent: Mar. 27, 2001

(54) THROMBIN INHIBITORY AGENTS AND METHODS OF USING SAME

(75) Inventors: Frank C. Church; Susannah J. Bauman, both of Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/257,581

(22) Filed: Feb. 25, 1999

Related U.S. Application Data

(60) Provisional application No. 60/076,210, filed on Feb. 27, 1998.

(51) Int. Cl.$^7$ .............................. C12P 21/04; C12P 21/06; C12N 1/20; C12N 15/00; C07H 21/04

(52) U.S. Cl. ................... 435/69.7; 435/69.1; 435/252.3; 435/320.1; 536/23.5; 800/13

(58) Field of Search ......................... 536/23.5; 435/69.1, 435/252.3, 320.1, 440, 69.7; 800/13; 514/12

(56) References Cited

U.S. PATENT DOCUMENTS 5,102,995  4/1992  Tollefsen et al. .
5,118,793  6/1992  Tollefsen et al. .

FOREIGN PATENT DOCUMENTS

0424351 A2  4/1991  (EP) .

OTHER PUBLICATIONS

Ngu et al (V) The protein folding Problem and Tertiary Structure Prediction (1994) Merz et al. (ed) Birkhauser, Boston, MA p. 433 and 492–95, 1994.*
Merriam Webster's Collegiate Dictionary, 10th Edition, Merriam–Webster Inc., USA pp. 906 and 1192, 1994.*
Ciaccia et al.; Heparin Promotes Proteolytic Inactivation by Thrombin of a Reactive Site Mutant (L444R) of Recombinant Heparin Cofactor II*, The Journal of Biological Chemistry 272:2 888–893 (1997).
Herzog et al.; Complete Nucleotide Sequence of the Gene for Human Heparin Cofactor II and Mapping to Chromosomal Band 22q11$^{+,‡}$, Biochemistry 30:5 1350–1357 (1991).
Hochuli et al.; Genetic Approach to Facilitate Purification of Recombinant Proteins with a Novel Metal Chelate Adsorbent, Biotechnology 6:11 1321–1325 (Nov. 1988).
Hochuli; Purification or Recombinant Proteins with Metal Chelate Adsorbent, Genetic Engineering 12:87–98 (1990).
International Search Report, PCT/US99/04137, Date of Mailing Aug. 4, 1999.
Bauman et al.; "Serpindipity": Enhanced Antithrombotic Activity of a Novel Recombinant Heparin Cofactor II, Blood, 92: 10 Part 2 of 2, (1988).

Bauman et al; Enchanced Antithrombotic Porperties of Heparin Cofactor II Through Site–Directed Mutagenesis, Experimental Biology '98 Meeting, Apr. 1998, SanFrancisco, CA, FASEB J. 12:5 Part II, A954 (Abstr. #5528) (1998).
Berthold et al.; Purification of Recombinant Antigenic Epitopes of the Human 68–kDa (U1) Ribonucleoprotein Antigen Using the Expression System pH6EX3 Followed by Metal Chelating Affinity Chromatography; Protein Expr. Purif. 1992 Feb.; 3(1):50–6.
Chen et al.; Expression Vector for Affinity Purification and Radiolabeling of Proteins Using *Escherichia coli* as Host; Gene 1994 Feb. 11;139(1):73–5 .
Church et al; Heparin–Binding Proteins Linking Hemostasis and Inflammation; TCM; 4:3 (1994) 140–146.
Ciaccia et al.; Determinants of Heparin Cofactor II Specificity for Thrombin; Protein and Peptide Letters, 4:4 215–224, (1997).
Crowe et al.; 6×His–Ni–NTA Chromatography as a Superior Technique in Recombinant Protein Expression/Purification; Methods Mol Biol (1994) 31:371–87.
Gettins et al.; Structure and Mechanism of Action of Serpins; Hematology/Oncology Clinics of North America, 6:6 Dec. 6 1992, 1393–1408.
Hopkins et al.; Inhibitory Mechanism of Serpins; The Journal of Biological Chemistry, 272:7 Feb. 14, 1997, 3905–3909.
Jensen et al.; The Role of Thrombin in the Thrombotic Process; Clinical Hemostasis Review, 6:8 Aug. 1992. p. 1–4.
Nachman et al.; :Hypercoagulable States; Ann Intern Med. 1993;119:819–827.
Patston et al.; A Database of Recombinant Wild–type and Mutant Serpins*; F.K. Schattauer Verlagsgesellschaft mbH (Stuttgart) 72(2):166–79 (1994).

(List continued on next page.)

*Primary Examiner*—David Saunders
*Assistant Examiner*—Amy DeCloux
(74) *Attorney, Agent, or Firm*—Myers Bigel Sibley & Sajovec, P.A.

(57) ABSTRACT

The present invention describes heparin cofactor II mutants comprising a carboxyl-terminal amino acid extension with enhanced anti-thrombotic effects. Preferred are amino acid extensions comprising His of from about 2 to 20 amino acids. Most preferred are heparin cofactor II proteins comprising (His)$_6$ and (His)$_5$Pro carboxyl terminal extensions. Further described are isolated nucleic acids encoding the inventive heparin cofactor II mutants, and vectors and host cells containing the same. Also provided are pharmaceutical formulations containing the inventive heparin cofactor II mutants, preferably in the presence of a polyanion cofactor. As another aspect of the present invention are methods of inhibiting thrombin activity so as to inhibit blood coagulation, regulate wound healing, tissue repair, and/or inhibit inflammation in a subject in need thereof.

41 Claims, 12 Drawing Sheets

OTHER PUBLICATIONS

Pratt et al.; Physicochemical Aspects of Herparin Cofactor II$^a$; Annals of the New York Academy of Sciences, 556: 104–155 (1989).

Pratt et al.; A Comparison of Three Heparin–binding Serine Proteinase Inhibitors*; The Journal of Biological Chemistry, 297:13 8795–8801, May 5, 1992.

Pratt et al.; General Features of the Heparin–binding Serpins Antithrombin, Heparin Cofactor II and Protein C Inhibitor*; Blood Coagulation and Fibrinolysis, 4, 479–490 (1993).

Quan et al.; Granzyme B is Inhibited by the Cowpox Virus Serpin Cytokine Response Modifier A*; The Journal of Biological Chemistry 270:18 10377–10379 May 5, 1995.

Roberts et al.; New Perspectives on the Coagulation Cascade; Hospital Practice, Jan. 15, 1992, 97–112.

Schmitt et al.; Affinity Purification of Histidine–tagged Proteins; Mol Biol Rep 1993 Oct; 18(3):223–30.

Sheehan et al.; Heparin Cofactor II is Regulated Allosterically and Not Primarily by Template Effects. Studies With Mutant Thrombins and Glycosoaminoglycans.; J Biol Chem 1994 Dec. 30;269(52):32747–32751.

Stone; Thrombin Inhibitors A New Generation of Antithrombotics; TCM 5:4 (1995) 134–140.

Stubbs et al.; The Clot Thickens: Clues Provided by Thrombin Structure; 1995 Elsevier Science Ltd., vol. 20(1) p. 23–28.

Tewari et al.; Yama/CPP32β, a Mammalian Homolof of CED–3, is a CrmA–Inhibitable Protease the Cleaves the Death Substrate Poly(ADP–Ribose) Polymerase; Cell, 81:801–809 Jun. 2, 1995.

Whinna et al.; Interaction of thrombin with Antithrombin, Heparin Cofactor II, and Protein C Inhibitor; Journal of Protein Chemistry, 12:6 (1993) 677–688.

* cited by examiner

```
         -48             -38             -28             -18              -8               3
          *               *               *               *               *               *
ATG AAA CAC TCA TTA AAC GCA CTT CTC ATT TTC CTC ATC ATA ACA TCT GCG TGG GGT GGG
Met Lys His Ser Leu Asn Ala Leu Leu Ile Phe Leu Ile Ile Thr Ser Ala Trp Gly Gly>

13              23              33              43              53              63
          *               *               *               *               *               *
AGC AAA GGC CCG CTG GAT CAG CTA GAG AAA GGA GGG GAA ACT GCT CAG TCT GCA GAT CCC
Ser Lys Gly Pro Leu Asp Gln Leu Glu Lys Gly Gly Glu Thr Ala Gln Ser Ala Asp Pro>

73              83              93             103             113             123
          *               *               *               *               *               *
CAG TGG GAG CAG TTA AAT AAC AAA AAC CTG AGC ATG AGC CTT CTC CCT GCC GAC TTC CAC
Gln Trp Glu Gln Leu Asn Asn Lys Asn Leu Ser Met Pro Leu Leu Pro Ala Asp Phe His>

133             143             153             163             173             183
          *               *               *               *               *               *
AAG GAA AAC ACC GTC ACC AAC GAC ATT CCA GAG GGG GAG GAG GAC GAC TAT CTG
Lys Glu Asn Thr Val Thr Asn Asp Ile Pro Glu Gly Glu Glu Asp Asp Tyr Leu>

193             203             213             223             233             243
          *               *               *               *               *               *
GAC CTG GAG AAG ATA TTC AGT GAA GAC GAC GAC TAC ATC GTC GAC AGT CTG TCA
Asp Leu Glu Lys Ile Phe Ser Glu Asp Asp Asp Tyr Ile Val Asp Ser Leu Ser>

253             263             273             283             293             303
          *               *               *               *               *               *
GTT TCC CCG ACA GAC TCT GAT GTG AGT GCT GGG AAC ATC CTC CAG CTT TTT CAT GGC AAG
Val Ser Pro Thr Asp Ser Asp Val Ser Ala Gly Asn Ile Leu Gln Leu Phe His Gly Lys>

313             323             333             343             353             363
          *               *               *               *               *               *
AGC CGG ATC CAG CGT CTT AAC ATC CTC AAC GCC AAG TTC GCT TTC AAC CTC TAC CGA GTG
Ser Arg Ile Gln Arg Leu Asn Ile Leu Asn Ala Lys Phe Ala Phe Asn Leu Tyr Arg Val>

373             383             393             403             413             423
          *               *               *               *               *               *
CTG AAA GAC CAG GTC AAC ACT TTC GAT AAC ATC ATA GCA CCC GTT GGC ATT TCT ACT
Leu Lys Asp Gln Val Asn Thr Phe Asp Asn Ile Ile Ala Pro Val Gly Ile Ser Thr>
```

FIG. 1A.

```
        433         443         453         463         473         483
          *           *           *           *           *           *
GCG ATG GGT ATG ATT TCC TTA GGC CTG AAG GGA GAG ACC CAT GAA CAA GTG CAC TCG ATT
Ala Met Gly Met Ile Ser Leu Gly Leu Lys Gly Glu Thr His Glu Gln Val His Ser Ile>

493         503         513         523         533         543
          *           *           *           *           *           *
TTG CAT TTT AAA GAC TTT GTT AAT GCT AGC AGC AAG TAT GAA ATC ACG ACC ATT CAT AAT
Leu His Phe Lys Asp Phe Val Asn Ala Ser Ser Lys Tyr Glu Ile Thr Thr Ile His Asn>

553         563         573         583         593         603
          *           *           *           *           *           *
CTC TTC CGT AAG CTG ACT CAT CGC CTC TTC AGG AAT TTT GGG TAC ACA CTG CGG TCA
Leu Phe Arg Lys Leu Thr His Arg Leu Phe Arg Arg Asn Phe Gly Tyr Thr Leu Arg Ser>

613         623         633         643         653         663
          *           *           *           *           *           *
GTC AAT GAC CTT TAT ATC CAG AAG CAG TTT CCA ATC CTG CTT GAC TTC AGA ACT AAA GTA
Val Asn Asp Leu Tyr Ile Gln Lys Gln Phe Pro Ile Leu Leu Asp Phe Arg Thr Lys Val>

673         683         693         703         713         723
          *           *           *           *           *           *
AGA GAG TAT TAC TTT GCT GAG GCC CAG ATA GCT GAC TTC TCA GAC CCT GCC TTC ATA TCA
Arg Glu Tyr Tyr Phe Ala Glu Ala Gln Ile Ala Asp Phe Ser Asp Pro Ala Phe Ile Ser>

733         743         753         763         773         783
          *           *           *           *           *           *
AAA ACC AAC AAC CAC ATC ATG AAG ATG CTC ACC AAG GGC CTC ATA AAA GAT GCT CTG GAG AAT
Lys Thr Asn Asn His Ile Met Lys Met Leu Thr Lys Gly Leu Ile Lys Asp Ala Leu Glu Asn>

793         803         813         823         833         843
          *           *           *           *           *           *
ATA GAC CCT GCT ACC CAG ATG ATG ATT CTC AAC TGC ATC TAC TTC AAA GGA TCC TGG GTG
Ile Asp Pro Ala Thr Gln Met Met Ile Leu Asn Cys Ile Tyr Phe Lys Gly Ser Trp Val>

853         863         873         883         893         903
          *           *           *           *           *           *
AAT AAA TTC CCA GTG GAA ATG ACA CAC AAC CAC TTC CGG CTG AAT GAG AGA GAG GTA
Asn Lys Phe Pro Val Glu Met Thr His Asn His Asn Phe Arg Leu Asn Glu Arg Glu Val>
```

```
         913                 923                 933                 943                 953                 963
          *                   *                   *                   *                   *                   *
GTT AAG GTT TCC ATG ATG CAG ACC CAG AAG GGG AAC TTC CTC GCA AAT GCA AAT GAC CAG GAG CTG
Val Lys Val Ser Met Met Gln Thr Gln Lys Gly Asn Phe Leu Ala Ala Asn Asp Gln Glu Leu>

973                 983                 993                1003                1013                1023
          *                   *                   *                   *                   *                   *
GAC TGC GAC ATC CTC CAG CTG GAA TAC GTG GGG GGC ATC AGC ATG CTA ATT GTG GTC CCA
Asp Cys Asp Ile Leu Gln Leu Glu Tyr Val Gly Gly Ile Ser Met Leu Ile Val Val Pro>

1033                1043                1053                1063                1073                1083
          *                   *                   *                   *                   *                   *
CAC AAG ATG TCT GGG ATG AAG ACC CTC GAA GCG CAA CTG ACA CCC CGG GTG GTG GAG AGA
His Lys Met Ser Gly Met Lys Thr Leu Glu Ala Gln Leu Thr Pro Arg Val Val Glu Arg>

1093                1103                1113                1123                1133                1143
          *                   *                   *                   *                   *                   *
TGG CAA AAA AGC ATG ACA AAC AGA ACT CGA GAA GTG CTT CTG CCG AAA TTC AAG CTG GAG
Trp Gln Lys Ser Met Thr Asn Arg Thr Arg Glu Val Leu Leu Pro Lys Phe Lys Leu Glu>

1153                1163                1173                1183                1193                1203
          *                   *                   *                   *                   *                   *
AAG TAC AAT CTA GTG GAG TCC CTT AAG TTG ATG GGG ATC AGG ATG CTG TTT GAC AAA
Lys Asn Tyr Asn Leu Val Glu Ser Leu Lys Leu Met Gly Ile Arg Met Leu Phe Asp Lys>

1213                1223                1233                1243                1253                1263
          *                   *                   *                   *                   *                   *
AAT GGC AAC ATG GCA GGC ATC TCA GAC CAA AGG ATC GCC ATC GAC CTG TTC AAG CAC CAA
Asn Gly Asn Met Ala Gly Ile Ser Asp Gln Arg Ile Ala Ile Asp Leu Phe Lys His Gln>

1273                1283                1293                1303                1313                1323
          *                   *                   *                   *                   *                   *
GGC ACG ATC ACA GTG AAC GAG GAA GGC ACC CAA ACC ACT GTG ACC ACG GTG GGG TTC
Gly Thr Ile Thr Val Asn Glu Glu Gly Thr Gln Ala Thr Thr Val Thr Thr Val Gly Phe>

1333                1343                1353                1363                1373                1383
          *                   *                   *                   *                   *                   *
ATG CCG CTG TCC ACC CAA GTC CGC TTC ACT GTC GAC CGC CCC TTT CTT TTC CTC ATC TAC
Met Pro Leu Ser Thr Gln Val Arg Phe Thr Val Asp Arg Pro Phe Leu Phe Leu Ile Tyr>
```

```
           1393        1403        1413        1423        1433        1443
      *     *     *     *     *     *     *     *     *     *     *     *
     GAG CAC CGC ACC AGC TGC CTG CTC TTC ATG GGA AGA GTG GCC AAC CCC AGC AGG TCC CAC
     Glu His Arg Thr Ser Cys Leu Leu Phe Met Gly Arg Val Ala Asn Pro Ser Arg Ser His>

1453
      *     *     *
     CAC CAC CAC CAC CAC TAG
     His His His His His ***>
```

FIG. 1D.

```
        -48            -38            -28            -18             -8              3
         *              *              *              *              *              *
ATG AAA CAC TCA TTA AAC GCA CTT CTC ATT TTC CTC ATA ACA TCT GCG TGG GGT GGG
Met Lys His Ser Leu Asn Ala Leu Leu Ile Phe Leu Ile Thr Ser Ala Trp Gly Gly>

13             23             33             43             53             63
         *              *              *              *              *              *
AGC AAA GGC CCG GAT CAG GAG AAA GGA GGG GAA ACT GCT CAG TCT GCA GAT CCC
Ser Lys Gly Pro Asp Gln Glu Lys Gly Gly Glu Thr Ala Gln Ser Ala Asp Pro>

73             83             93            103            113            123
         *              *              *              *              *              *
CAG TGG GAG CAG TTA AAT AAC AAA AAC AGC CCT CTT CTC CCT GCC GAC TTC CAC
Gln Trp Glu Gln Leu Asn Asn Lys Asn Ser Met Pro Leu Leu Pro Ala Asp Phe His>

133            143            153            163            173            183
         *              *              *              *              *              *
AAG GAA AAC ACC GTC ACC GAC AAC GAC TGG ATT CCA GAG GGG GAG GAC GAC TAT CTG
Lys Glu Asn Thr Val Thr Asp Asn Asp Trp Ile Pro Glu Gly Glu Asp Asp Tyr Leu>

193            203            213            223            233            243
         *              *              *              *              *              *
GAC CTG GAG AAG TTC AGT GAA GAC GAC TAC GAC GAC ATC GTC GAC AGT TCA
Asp Leu Glu Lys Phe Ser Glu Asp Asp Tyr Asp Asp Ile Val Asp Ser Ser>

253            263            273            283            293            303
         *              *              *              *              *              *
GTT TCC CCG ACA GAC TCT GAT GTG AGT GCT GGG AAC ATC CTC CAG CTT TTT CAT GGC AAG
Val Ser Pro Thr Asp Ser Asp Val Ser Ala Gly Asn Ile Leu Gln Leu Phe His Gly Lys>

313            323            333            343            353            363
         *              *              *              *              *              *
AGC CGG ATC CAG CGT CTT AAC ATC CTC AAC GCC AAG TTC GCT TTC AAC CTC TAC CGA GTG
Ser Arg Ile Gln Arg Leu Asn Ile Leu Asn Ala Lys Phe Ala Phe Asn Leu Tyr Arg Val>

373            383            393            403            413            423
         *              *              *              *              *              *
CTG AAA GAC CAG GAC GTC AAC ACT TTC GAT AAC ATC TTC ATA GCA CCC GTT GGC ATT TCT ACT
Leu Lys Asp Gln Asp Val Asn Thr Phe Asp Asn Ile Phe Ile Ala Pro Val Gly Ile Ser Thr>
```

FIG. 4A.

```
          433         443         453         463         473         483
           *           *           *           *           *           *
GCG ATG GGT ATG ATT TCC TTA GGC CTG AAG GGA GAG ACC CAT GAA CAA GTG CAC TCG ATT
Ala Met Gly Met Ile Ser Leu Gly Leu Lys Gly Glu Thr His Glu Gln Val His Ser Ile>

493         503         513         523         533         543
           *           *           *           *           *           *
TTG CAT TTT AAA GAC TTT GTT AAT GCT AGC AGC TAT GAA ATC ACG ACC ATT CAT AAT
Leu His Phe Lys Asp Phe Val Asn Ala Ser Ser Tyr Glu Ile Thr Thr Ile His Asn>

553         563         573         583         593         603
           *           *           *           *           *           *
CTC TTC CGT AAG CTG ACT CAT CGC CTC TTC AGG AGG AAT TTT GGG TAC ACA CTG CGG TCA
Leu Phe Arg Lys Leu Thr His Arg Leu Phe Arg Arg Asn Phe Gly Tyr Thr Leu Arg Ser>

613         623         633         643         653         663
           *           *           *           *           *           *
GTC AAT GAC CTT TAT ATC CAG AAG CAG TTT CCA ATC CTG CTT GAC TTC AGA ACT AAA GTA
Val Asn Asp Leu Tyr Ile Gln Lys Gln Phe Pro Ile Leu Leu Asp Phe Arg Thr Lys Val>

673         683         693         703         713         723
           *           *           *           *           *           *
AGA GAG TAT TAC TTT GCT GAG GCC CAG ATA GCT GAC TTC TCA GAC CCT GCC TTC ATA TCA
Arg Glu Tyr Tyr Phe Ala Glu Ala Gln Ile Ala Asp Phe Ser Asp Pro Ala Phe Ile Ser>

733         743         753         763         773         783
           *           *           *           *           *           *
AAA ACC AAC ATC ATG AAG CTC ATA AAA GAT GCT CTG GAG AAT
Lys Thr Asn Ile Met Lys Leu Thr Lys Gly Leu Ile Lys Asp Ala Leu Glu Asn>

793         803         813         823         833         843
           *           *           *           *           *           *
ATA GAC CCT GCT ACC CAG ATG ATG ATT CTC AAC TGC ATC TAC TTC AAA GGA TCC TGG GTG
Ile Asp Pro Ala Thr Gln Met Met Ile Leu Asn Cys Ile Tyr Phe Lys Gly Ser Trp Val>

853         863         873         883         893         903
           *           *           *           *           *           *
AAT AAA TTC CCA GAA ATG ACA CAC AAC CAC TTC CGG CTG AAT GAG AGA GAG GTA
Asn Lys Phe Pro Val Glu Met Thr His Asn His Asn Phe Arg Leu Asn Glu Arg Glu Val>
```

```
       913         923         933         943         953         963
         *           *           *           *           *           *
GTT AAG GTT TCC ATG ATG CAG ACC ATG AAG GGG AAC TTC CTC GCA GCA AAT GAC CAG GAG CTG
Val Lys Val Ser Met Met Gln Thr Met Lys Gly Asn Phe Leu Ala Ala Asn Asp Gln Glu Leu>

973         983         993        1003        1013        1023
         *           *           *           *           *           *
GAC TGC GAC ATC CTC CAG CTG GAA CTG GTG GGG GGC ATG AGC ATG CTA ATT GTG GTC CCA
Asp Cys Asp Ile Leu Gln Leu Glu Leu Val Gly Gly Tyr Val Gly Ile Ser Met Leu Ile Val Val Pro>

1033        1043        1053        1063        1073        1083
         *           *           *           *           *           *
CAC AAG ATG TCT GGG ATG AAG ACC CTC GAA GCG CAA CTG ACA CCC CGG GTG GTG GAG AGA
His Lys Met Ser Gly Met Lys Thr Leu Glu Ala Gln Leu Thr Pro Arg Val Val Glu Arg>

1093        1103        1113        1123        1133        1143
         *           *           *           *           *           *
TGG CAA AAA AGC ATG AAC ACT CGA GAA GTG CTT CTG CCG AAA TTC AAG CTG GAG
Trp Gln Lys Ser Met Thr Asn Arg Thr Arg Glu Val Leu Leu Pro Lys Phe Lys Leu Glu>

1153        1163        1173        1183        1193        1203
         *           *           *           *           *           *
AAG AAC TAC AAT CTA GTG GAG TCC CTT AAG TTG ATG GGG ATC AGG ATG CTG TTT GAC AAA
Lys Asn Tyr Asn Leu Val Glu Ser Leu Lys Leu Met Gly Ile Arg Met Leu Phe Asp Lys>

1213        1223        1233        1243        1253        1263
         *           *           *           *           *           *
AAT GGC AAC ATG GCA GGA ATC TCA GAC CAA AGG ATC GCC ATC GAC CTG TTC AAG CAC CAA
Asn Gly Asn Met Ala Gly Ile Ser Asp Gln Arg Ile Ala Ile Asp Leu Phe Lys His Gln>

1273        1283        1293        1303        1313        1323
         *           *           *           *           *           *
GGC ACG ATC ACA GTG AAC GAG GAA GGC ACC CAA GCC ACC ACT GTG ACC ACG GTG GGG TTC
Gly Thr Ile Thr Val Asn Glu Glu Gly Thr Gln Ala Thr Thr Val Thr Thr Val Gly Phe>

1333        1343        1353        1363        1373        1383
         *           *           *           *           *           *
ATG CCG CTG TCC ACC CAA GTC CGC GGC TTC ACT GTC GAC CGC CCC TTT CTT TTC CTC TAC
Met Pro Leu Ser Thr Gln Val Arg Gly Phe Thr Val Asp Arg Pro Phe Leu Phe Leu Ile Tyr>
```

```
         1393        1403        1413        1423        1433        1443
    *      *     *      *     *      *     *      *     *      *     *      *
GAG CAC CGC ACC AGC TGC CTG CTC TTC ATG GGA AGA GTG GCC AAC CCC AGC AGG TCC CAC
Glu His Arg Thr Ser Cys Leu Leu Phe Met Gly Arg Val Ala Asn Pro Ser Arg Ser His>
        1453
    *      *
CAC CAC CAC CAC CCC TAG
His His His His Pro ***>
```

FIG. 4D.

SEQUENCE LISTING

<160> NUMBER OF SEQ ID NOS: 7

<210> SEQ ID NO 1
<211> LENGTH: 54
<212> TYPE: DNA

```
<213> ORGANISM: Artificial Sequence
<220> FEATURE:
<223> OTHER INFORMATION: Description of Artificial Sequence:primer

<400> SEQUENCE: 1
gccaacccca gcaggtccca ccaccaccac caccactaga ggtggaggtc tagg          54

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 2
ggggttcatg ccgcggtcca cccaagtccg                                     30

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence:primer

<400> SEQUENCE: 3
ggtgcaaaga ataagaacat tttagtggtg gtggtggtgg tgcttaacac aagggttggc    60

<210> SEQ ID NO 4
<211> LENGTH: 1518
<212> TYPE: DNA
<213> ORGANISM: Homo sapiens

<400> SEQUENCE: 4
atgaaacact cattaaacgc acttctcatt ttcctcatca taacatctgc gtggggtggg    60
agcaaaggcc cgctggatca gctagagaaa ggagggaaa ctgctcagtc tgcagatccc    120
cagtgggagc agttaaataa caaaaacctg agcatgcctc ttctccctgc cgacttccac    180
aaggaaaaca ccgtcaccaa cgactggatt ccagaggggg aggaggacga cgactatctg    240
gacctggaga agatattcag tgaagacgac gactacatcg acatcgtcga cagtctgtca    300
gtttccccga cagactctga tgtgagtgct gggaacatcc tccagctttt tcatggcaag    360
agccggatcc agcgtcttaa catcctcaac gccaagttcg ctttcaacct ctaccgagtg    420
ctgaaagacc aggtcaacac tttcgataac atcttcatag cacccgttgg catttctact    480
gcgatgggta tgatttcctt aggcctgaag ggagagaccc atgaacaagt gcactcgatt    540
ttgcatttta aagactttgt taatgctagc agcaagtatg aaatcacgac cattcataat    600
ctcttccgta agctgactca tcgcctcttc aggaggaatt ttgggtacac actgcggtca    660
gtcaatgacc tttatatcca gaagcagttt ccaatcctgc ttgacttcag aactaaagta    720
agagagtatt actttgctga ggcccagata gctgacttct cagaccctgc cttcatatca    780 aaaccaaca accacatcat gaagctcacc aagggcctca taaagatgc tctggagaat    840 atagaccctg ctacccagat gatgattctc aactgcatct acttcaaagg atcctgggtg    900
aataaattcc cagtggaaat gacacacaac cacaacttcc ggctgaatga gagagaggta    960
gttaaggttt ccatgatgca gaccaagggg aacttcctcg cagcaaatga ccaggagctg    1020
gactgcgaca tcctccagct ggaatacgtg gggggcatca gcatgctaat tgtggtccca    1080
cacaagatgt ctgggatgaa gaccctcgaa gcgcaactga cccccggt ggtggagaga    1140 tggcaaaaaa gcatgacaaa cagaactcga gaagtgcttc tgccgaaatt caagctggag    1200
```

-continued

```
aagaactaca atctagtgga gtcccttaag ttgatgggga tcaggatgct gtttgacaaa      1260
aatggcaaca tggcaggcat ctcagaccaa aggatcgcca tcgacctgtt caagcaccaa      1320
ggcacgatca cagtgaacga ggaaggcacc caagccacca ctgtgaccac ggtggggttc      1380
atgccgctgt ccacccaagt ccgcttcact gtcgaccgcc cctttctttt cctcatctac      1440
gagcaccgca ccagctgcct gctcttcatg ggaagagtgg ccaaccccag caggtcccac      1500
caccaccacc accactag                                                   1518
```

<210> SEQ ID NO 5
<211> LENGTH: 505
<212> TYPE: PRT
<213> ORGANISM: Homo sapiens

<400> SEQUENCE: 5

```
Met Lys His Ser Leu Asn Ala Leu Leu Ile Phe Leu Ile Ile Thr Ser
  1               5                  10                  15

Ala Trp Gly Gly Ser Lys Gly Pro Leu Asp Gln Leu Glu Lys Gly Gly
             20                  25                  30

Glu Thr Ala Gln Ser Ala Asp Pro Gln Trp Glu Gln Leu Asn Asn Lys
         35                  40                  45

Asn Leu Ser Met Pro Leu Leu Pro Ala Asp Phe His Lys Glu Asn Thr
     50                  55                  60

Val Thr Asn Asp Trp Ile Pro Glu Gly Glu Asp Asp Asp Tyr Leu
 65                  70                  75                  80

Asp Leu Glu Lys Ile Phe Ser Glu Asp Asp Tyr Ile Asp Ile Val
                 85                  90                  95

Asp Ser Leu Ser Val Ser Pro Thr Asp Ser Asp Val Ser Ala Gly Asn
            100                 105                 110

Ile Leu Gln Leu Phe His Gly Lys Ser Arg Ile Gln Arg Leu Asn Ile
        115                 120                 125

Leu Asn Ala Lys Phe Ala Phe Asn Leu Tyr Arg Val Leu Lys Asp Gln
    130                 135                 140

Val Asn Thr Phe Asp Asn Ile Phe Ile Ala Pro Val Gly Ile Ser Thr
145                 150                 155                 160

Ala Met Gly Met Ile Ser Leu Gly Leu Lys Gly Glu Thr His Glu Gln
                165                 170                 175

Val His Ser Ile Leu His Phe Lys Asp Phe Val Asn Ala Ser Ser Lys
            180                 185                 190

Tyr Glu Ile Thr Thr Ile His Asn Leu Phe Arg Lys Leu Thr His Arg
        195                 200                 205

Leu Phe Arg Arg Asn Phe Gly Tyr Thr Leu Arg Ser Val Asn Asp Leu
    210                 215                 220

Tyr Ile Gln Lys Gln Phe Pro Ile Leu Leu Asp Phe Arg Thr Lys Val
225                 230                 235                 240

Arg Glu Tyr Tyr Phe Ala Glu Ala Gln Ile Ala Asp Phe Ser Asp Pro
                245                 250                 255

Ala Phe Ile Ser Lys Thr Asn Asn His Ile Met Lys Leu Thr Lys Gly
            260                 265                 270

Leu Ile Lys Asp Ala Leu Glu Asn Ile Asp Pro Ala Thr Gln Met Met
        275                 280                 285

Ile Leu Asn Cys Ile Tyr Phe Lys Gly Ser Trp Val Asn Lys Phe Pro
    290                 295                 300

Val Glu Met Thr His Asn His Asn Phe Arg Leu Asn Glu Arg Glu Val
```

| | | | | | | | | | | | | | | |
|---|---|---|---|---|---|---|---|---|---|---|---|---|---|---|
| | | | | 305 | | | | 310 | | | | 315 | | 320 |
| Val | Lys | Val | Ser | Met | Met | Gln | Thr | Lys | Gly | Asn | Phe | Leu | Ala | Asn |
| | | | | 325 | | | | 330 | | | | 335 | | |
| Asp | Gln | Glu | Leu | Asp | Cys | Asp | Ile | Leu | Gln | Leu | Glu | Tyr | Val | Gly | Gly |
| | | | 340 | | | | | 345 | | | | | 350 | | |
| Ile | Ser | Met | Leu | Ile | Val | Val | Pro | His | Lys | Met | Ser | Gly | Met | Lys | Thr |
| | | | 355 | | | | | 360 | | | | | 365 | | |
| Leu | Glu | Ala | Gln | Leu | Thr | Pro | Arg | Val | Val | Glu | Arg | Trp | Gln | Lys | Ser |
| | | | 370 | | | | | 375 | | | | | 380 | | |
| Met | Thr | Asn | Arg | Thr | Arg | Glu | Val | Leu | Leu | Pro | Lys | Phe | Lys | Leu | Glu |
| 385 | | | | | 390 | | | | | 395 | | | | | 400 |
| Lys | Asn | Tyr | Asn | Leu | Val | Glu | Ser | Leu | Lys | Leu | Met | Gly | Ile | Arg | Met |
| | | | | 405 | | | | | 410 | | | | | 415 | |
| Leu | Phe | Asp | Lys | Asn | Gly | Asn | Met | Ala | Gly | Ile | Ser | Asp | Gln | Arg | Ile |
| | | | | 420 | | | | | 425 | | | | | 430 | |
| Ala | Ile | Asp | Leu | Phe | Lys | His | Gln | Gly | Thr | Ile | Thr | Val | Asn | Glu | Glu |
| | | | | 435 | | | | | 440 | | | | | 445 | |
| Gly | Thr | Gln | Ala | Thr | Thr | Val | Thr | Val | Gly | Phe | Met | Pro | Leu | Ser | |
| | | | | 450 | | | | | 455 | | | | | 460 | |
| Thr | Gln | Val | Arg | Phe | Thr | Val | Asp | Arg | Pro | Phe | Leu | Phe | Leu | Ile | Tyr |
| 465 | | | | | 470 | | | | | 475 | | | | | 480 |
| Glu | His | Arg | Thr | Ser | Cys | Leu | Leu | Phe | Met | Gly | Arg | Val | Ala | Asn | Pro |
| | | | | 485 | | | | | 490 | | | | | 495 | |
| Ser | Arg | Ser | His | His | His | His | His | | | | | | | | |
| | | | | 500 | | | | | 505 | | | | | | |

<210> SEQ ID NO 6
<211> LENGTH: 1518
<212> TYPE: DNA
<213> ORGANISM: Homo sapiens

<400> SEQUENCE: 6

```
atgaaacact cattaaacgc acttctcatt ttcctcatca taacatctgc gtggggtggg      60
agcaaaggcc cgctggatca gctagagaaa ggaggggaaa ctgctcagtc tgcagatccc     120
cagtgggagc agtaaataa caaaaacctg agcatgcctc ttctccctgc cgacttccac     180
aaggaaaaca ccgtcaccaa cgactggatt ccagaggggg aggaggacga cgactatctg     240
gacctggaga agatattcag tgaagacgac gactacatcg acatcgtcga cagtctgtca     300
gtttccccga cagactctga tgtgagtgct gggaacatcc tccagctttt tcatggcaag     360
agccggatcc agcgtcttaa catcctcaac gccaagttcg ctttcaacct ctaccgagtg     420
ctgaaagacc aggtcaacac tttcgataac atcttcatag cacccgttgg catttctact     480
gcgatgggta tgatttcctt aggcctgaag ggagagaccc atgaacaagt gcactcgatt     540
ttgcatttta aagactttgt taatgctagc agcaagtatg aaatcacgac cattcataat     600
ctcttccgta agctgactca tcgcctcttc aggaggaatt tgggtacac actgcggtca     660
gtcaatgacc tttatatcca gaagcagttt ccaatcctgc ttgacttcag aactaaagta     720
agagagtatt actttgctga ggcccagata gctgacttct cagaccctgc cttcatatca     780
aaaaccaaca accacatcat gaagctcacc aagggcctca taaagatgc tctggagaat     840
atagaccctg ctacccagat gatgattctc aactgcatct acttcaaagg atcctgggtg     900
aataaattcc cagtggaaat gacacacaac cacaacttcg gctgaatga gagagaggta     960
gttaaggttt ccatgatgca gaccaagggg aacttcctcg cagcaaatga ccaggagctg    1020
```

```
gactgcgaca tcctccagct ggaatacgtg gggggcatca gcatgctaat tgtggtccca   1080
cacaagatgt ctgggatgaa gaccctcgaa gcgcaactga cacccgggt ggtggagaga   1140 tggcaaaaaa gcatgacaaa cagaactcga gaagtgcttc tgccgaaatt caagctggag   1200
aagaactaca atctagtgga gtcccttaag ttgatgggga tcaggatgct gtttgacaaa   1260
aatggcaaca tggcaggcat ctcagaccaa aggatcgcca tcgacctgtt caagcaccaa   1320
ggcacgatca cagtgaacga ggaaggcacc caagccacca ctgtgaccac ggtggggttc   1380
atgccgctgt ccacccaagt ccgcttcact gtcgaccgcc cctttctttt cctcatctac   1440
gagcaccgca ccagctgcct gctcttcatg ggaagagtgg ccaaccccag caggtcccac   1500
caccaccacc acccctag                                                 1518
```

<210> SEQ ID NO 7
<211> LENGTH: 505
<212> TYPE: PRT
<213> ORGANISM: Homo sapiens

<400> SEQUENCE: 7

```
Met Lys His Ser Leu Asn Ala Leu Leu Ile Phe Leu Ile Ile Thr Ser
  1               5                  10                  15

Ala Trp Gly Gly Ser Lys Gly Pro Leu Asp Gln Leu Glu Lys Gly Gly
                 20                  25                  30

Glu Thr Ala Gln Ser Ala Asp Pro Gln Trp Glu Gln Leu Asn Asn Lys
             35                  40                  45

Asn Leu Ser Met Pro Leu Leu Pro Ala Asp Phe His Lys Glu Asn Thr
         50                  55                  60

Val Thr Asn Asp Trp Ile Pro Glu Gly Glu Asp Asp Asp Tyr Leu
 65                  70                  75                  80

Asp Leu Glu Lys Ile Phe Ser Glu Asp Asp Tyr Ile Asp Ile Val
                 85                  90                  95

Asp Ser Leu Ser Val Ser Pro Thr Asp Ser Asp Val Ser Ala Gly Asn
                100                 105                 110

Ile Leu Gln Leu Phe His Gly Lys Ser Arg Ile Gln Arg Leu Asn Ile
            115                 120                 125

Leu Asn Ala Lys Phe Ala Phe Asn Leu Tyr Arg Val Leu Lys Asp Gln
        130                 135                 140

Val Asn Thr Phe Asp Asn Ile Phe Ile Ala Pro Val Gly Ile Ser Thr
145                 150                 155                 160

Ala Met Gly Met Ile Ser Leu Gly Leu Lys Gly Glu Thr His Glu Gln
                165                 170                 175

Val His Ser Ile Leu His Phe Lys Asp Phe Val Asn Ala Ser Ser Lys
            180                 185                 190

Tyr Glu Ile Thr Thr Ile His Asn Leu Phe Arg Lys Leu Thr His Arg
        195                 200                 205

Leu Phe Arg Arg Asn Phe Gly Tyr Thr Leu Arg Ser Val Asn Asp Leu
    210                 215                 220

Tyr Ile Gln Lys Gln Phe Pro Ile Leu Leu Asp Phe Arg Thr Lys Val
225                 230                 235                 240

Arg Glu Tyr Tyr Phe Ala Glu Ala Gln Ile Ala Asp Phe Ser Asp Pro
                245                 250                 255

Ala Phe Ile Ser Lys Thr Asn Asn His Ile Met Lys Leu Thr Lys Gly
            260                 265                 270

Leu Ile Lys Asp Ala Leu Glu Asn Ile Asp Pro Ala Thr Gln Met Met
```

-continued

```
                    275                 280                 285
Ile Leu Asn Cys Ile Tyr Phe Lys Gly Ser Trp Val Asn Lys Phe Pro
        290                 295                 300

Val Glu Met Thr His Asn His Asn Phe Arg Leu Asn Glu Arg Glu Val
305                 310                 315                 320

Val Lys Val Ser Met Met Gln Thr Lys Gly Asn Phe Leu Ala Ala Asn
                325                 330                 335

Asp Gln Glu Leu Asp Cys Asp Ile Leu Gln Leu Glu Tyr Val Gly Gly
                340                 345                 350

Ile Ser Met Leu Ile Val Val Pro His Lys Met Ser Gly Met Lys Thr
                355                 360                 365

Leu Glu Ala Gln Leu Thr Pro Arg Val Val Glu Arg Trp Gln Lys Ser
        370                 375                 380

Met Thr Asn Arg Thr Arg Glu Val Leu Leu Pro Lys Phe Lys Leu Glu
385                 390                 395                 400

Lys Asn Tyr Asn Leu Val Glu Ser Leu Lys Leu Met Gly Ile Arg Met
                405                 410                 415

Leu Phe Asp Lys Asn Gly Asn Met Ala Gly Ile Ser Asp Gln Arg Ile
                420                 425                 430

Ala Ile Asp Leu Phe Lys His Gln Gly Thr Ile Thr Val Asn Glu Glu
                435                 440                 445

Gly Thr Gln Ala Thr Thr Val Thr Thr Val Gly Phe Met Pro Leu Ser
        450                 455                 460

Thr Gln Val Arg Phe Thr Val Asp Arg Pro Phe Leu Phe Leu Ile Tyr
465                 470                 475                 480

Glu His Arg Thr Ser Cys Leu Leu Phe Met Gly Arg Val Ala Asn Pro
                485                 490                 495

Ser Arg Ser His His His His Pro
                500                 505
```

THROMBIN INHIBITORY AGENTS AND METHODS OF USING SAME

RELATED APPLICATION INFORMATION

This application claims the benefit of United States Provisional Application No. 60/076,210, filed Feb. 27, 1998, which is incorporated by reference herein in its entirety.

STATEMENT OF FEDERAL SUPPORT

This invention was made with government support under grant number RO1 HC32656-10 from the National Institute of Health. The government has certain rights to this invention.

FIELD OF THE INVENTION

The present invention provides compositions and methods for inhibiting thrombin. In particular, the present invention provides heparin cofactor II mutants and methods of administering the same that may be employed to inhibit thrombin action both in vitro and in vivo.

BACKGROUND OF THE INVENTION

The classic model of blood coagulation proposes a series of cascading reactions that result in clot formation. This model has been modified to incorporate initiation, amplification, and propagation phases. Furie and Furie, (1992) *N. Engl. J. Med.* 326:800; Roberts and Lozier, (1992) *Hosp. Pract.* 27:97. Adding an additional layer of complexity is an array of mechanisms that turn off and/or modulate the coagulation cascade. Thrombin is a key regulatory point in pathways that lead to blood coagulation, as well as those that reverse this process. Circulating prothrombin is cleaved to form thrombin following interaction with other blood clotting factors. Thrombin is a trypsin-like serine protease, which is responsible for the proteolytic conversion of fibrinogen to fibrin, with the aggregation of fibrin molecules resulting in the formation of a "soft" clot.

The proteolytic actions of thrombin are inhibited by interaction with plasma serine proteinase inhibitors ("serpins"), such as heparin cofactor II (HCII), antithrombin III (ATIII), protein C inhibitor (PCI), and α-proteinase inhibitor. Thrombin recognizes a conserved amino acid sequence among serpins, termed the "reactive site loop", as a potential substrate. Interaction of thrombin with the reactive site loop results in the formation of a thrombin-serpin complex that is essentially irreversible. Complex formation inactivates both the thrombin protease and serpin inhibitory activities. Pratt and Church, (1993) *Blood Coag. and Fibrinol.* 4:479.

The inhibitory actions of ATIII, PCI and HCII are accelerated in the presence of heparin (1000–10,000 fold), and the anti-coagulation effects of heparin are believed to be mediated through these plasma serpins. HCII is the most dependent of these inhibitors on glycosaminoglycan; it has only about 10% the inhibitory activity of ATIII or PCI in the absence of heparin. Pratt et al., (1989a) *Thromb. Res.* 53:595; Pratt et al., (1989) *Ann. N.Y. Acad. Sci.* 556:104; Pratt et al., (1992) *J. Biol. Chem.* 267:8795; Pratt and Church, (1992) *J. Biol. Chem.* 267:8789. Thrombin inhibition by HCII, but not ATIII, is also accelerated in the presence of dermatan sulfate and dermatan sulfate proteoglycans. Pratt and Church, (1993) *Blood Coag. Fibrinol.* 4:479. Moreover, ATIII inhibits most of the serine proteases involved in coagulation, whereas HCII appears to be uniquely specific for thrombin. Church and Hoffman, (1994) *TCM* 4:140. The only other known substrates for HCII are chymotrypsin, cathepsin G, and *Streptomyces gresius* Protease B. Church et al., (1985) *Proc. Natl. Acad. Sci. USA* 82:6431; Parker and Tollefsen, (1985) *J. Biol. Chem.* 260:3501; Pratt et al., (1989b) *Ann. N.Y. Acad. Sci.* 556:104.

As described above, heparin is a known anti-coagulant, and it is widely-administered to human and animal subjects for this purpose. Individual response to heparin is quite variable, however, and heparin administration can result in hemorrhaging, thrombocytopenia, and osteoporosis. Stone, (1995) *TCM* 5:134; U.S. Pat. Nos. 5,118,793 and 5,102,995 to Tollefsen et al. Accordingly, there exists a need in the art for alternative anti-coagulant agents and therapies.

SUMMARY OF THE INVENTION

Heparin cofactor II (HCII) is a serine protease inhibitor ("serpin") that acts to inhibit the biological actions of thrombin. The present invention is based on the discovery of novel HCII mutants with hyperactive thrombin inhibitory activity.

One aspect of the present invention is a mutant heparin cofactor II comprising, in combination, a heparin cofactor II and a carboxyl terminal amino acid extension, where the carboxyl terminal extension comprises at least one histidine residue and confers enhanced anti-thrombin activity to the mutant heparin cofactor II. Also provided are isolated DNA encoding the mutant heparin cofactor II, and vectors and host cells containing the same.

A further aspect of the present invention are pharmaceutical compositions comprising the inventive mutant heparin cofactor II molecules.

A further aspect of the present invention is a method of inhibiting blood coagulation in a subject in need thereof, comprising administering a mutant heparin cofactor II comprising a carboxyl terminal extension to the subject in an amount effective to inhibit blood coagulation, where the carboxyl terminal extension confers enhanced anti-coagulant activity to the heparin cofactor II.

Still a further aspect of the present invention is a method of inhibiting blood coagulation in a biological sample comprising adding a mutant heparin cofactor II comprising a carboxyl terminal extension to the biological sample in an amount effective to inhibit blood coagulation, where the carboxyl terminal extension confers enhanced anti-coagulant activity to the heparin cofactor II.

Yet a further aspect of the present invention is a method of regulating wound healing in a subject in need thereof, comprising administering a mutant heparin cofactor II comprising a carboxyl terminal extension to the subject in an amount effective to regulate wound healing, where the carboxyl terminal extension confers enhanced anti-thrombin activity to the heparin cofactor II.

As a further aspect, the present invention provides a method of regulating tissue repair in a subject in need thereof, comprising administering a mutant heparin cofactor II comprising a carboxyl terminal extension to the subject in an amount effective to regulate tissue repair, where the carboxyl terminal extension confers enhanced anti-thrombin activity to the heparin cofactor II.

As a further aspect, the present invention provides a method of inhibiting inflammation in a subject in need thereof, comprising administering a mutant heparin cofactor II comprising a carboxyl terminal extension to the subject in an amount effective to inhibit inflammation, where the carboxyl terminal extension confers enhanced anti-inflammatory activity to the heparin cofactor II.

BRIEF DESCRIPTION OF THE DRAWINGS

FIG. 1 shows the nucleotide (SEQ ID NO:4) and amino acid (SEQ ID NO:5) sequences of the rHCII-CHis$_6$ mutant. The (CAC)$_6$ sequence encoding the histidine tail was inserted directly before the TAG stop codon in the HCII sequence. The nucleotide sequence is shown from −57 to 1461, which encodes the sequences of the start codon, signal peptide, mature protein, and the stop codon.

FIG. 4 shows the nucleotide (SEQ ID NO:6) and amino acid (SEQ ID NO:7) sequences of the rHCII-CHis$_5$Pro mutant. The (CAC)$_5$CCC sequence encoding the histidine-proline tail was inserted directly before the TAG stop codon in the HCII sequence. The nucleotide sequence is shown from −57 to 1461, which encodes the sequences of the start codon, signal peptide, mature protein, and the stop codon.

DETAILED DESCRIPTION OF THE INVENTION

Figure 2A:
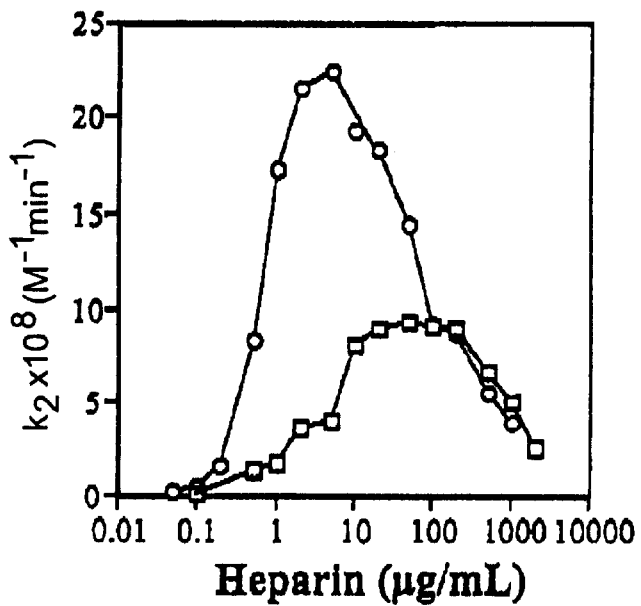
FIG. 2 is a graphical representation of the inhibition of thrombin by rHCII and rHCII-CHis$_6$ in the presence of heparin and dermatan sulfate. Thrombin inhibition assays in the presence of glycosaminoglycan were performed as detailed in Example 4 with plasma purified α-thrombin and increasing amounts of heparin (top panel) and dermatan sulfate (bottom panel) comparing wt-rHCII ❏ and rHCII-CHis$_6$ ◯. The curves shown are averages of two or three recombinant protein preps assayed two to three times each.

The present invention is based on the discovery of mutant heparin cofactor II (HCII) molecules with enhanced thrombin inhibitory activities. Also provided are isolated DNA sequences and vectors encoding the inventive HCII proteins, and host cells containing the same. The disclosed HCII mutants can be used to modulate thrombin activity, both in vitro and in vivo.

A. Heparin Cofactor II Mutants.

As demonstrated below, HCII mutants containing a carboxyl terminal extension can exhibit enhanced anti-thrombin activity. By "enhanced anti-thrombin activity" or "enhanced thrombin inhibitory activity", it is meant that the HCII mutant inhibits at least one biological action of thrombin to a greater extent than does wild-type HCII in the absence and/or presence of polyanions, such as glycosaminoglycans (e.g., heparin, heparan sulfate, dermatan sulfate, etc.).

In preferred embodiments of the invention, the carboxyl terminal extension is a sequence of amino acids (including modified amino acids, e.g., by post-translational modification, such as phosphorylation, methylation, amidation, and glycosylation). There is no particular upper or lower limit to the length of the extension, as long as the modified HCII molecule exhibits enhanced anti-thrombin activity. Preferred are extensions of about 2 to about 20 amino acids, more preferred are extensions of about 3 to about 12 amino acids, and yet more preferred are extensions of about 5 to about 8 amino acids. Most preferred are 6 amino acid carboxyl terminal extensions.

In particular preferred embodiments, the carboxyl terminal extension comprises at least one histidine residue. Alternatively, the carboxyl terminal extension comprises at least two, three, four, five, six, seven, eight, nine, or even ten histidine residues. It is not necessary that the histidine residues be a continuous sequence within the carboxyl terminal extension, i.e., there may be intervening amino acid residues. Alternatively stated, at least 5%, 10%, 20%, 30%, 40%, 50%, 60%, 70%, 80% or more of the amino acid residues in the carboxyl terminal extension are histidine residues. In other preferred embodiments, the carboxyl terminal extension comprises a carboxyl terminal proline. In more preferred embodiments, the carboxyl terminal extension consists of six histidine residues (i.e., —(His)$_6$—COOH) or 5 histidine residues and a proline residue, with the proline being the carboxyl terminal residue (i.e., —(His)$_5$Pro—COOH).

The present investigations have determined that carboxyl terminal extensions of six alanine or six lysine residues impair the activity of the resulting mutant HCII as compared with wild-type HCII. Accordingly, in particular preferred embodiments of the invention, less than 100%, 80%, 60%, 40%, or 20% of the amino acid residues in the carboxyl terminal extension are lysine residues. Alternatively, in other preferred embodiments, less than 100%, 80%, 60%, 40%, or 20% of the amino acid residues in the carboxyl terminal extension are alanine residues Suitable thrombin substrates may be any form of thrombin that interacts with HCII and is inhibited thereby. Examples include human, bovine, porcine, rat and mouse thrombins, and the like. "Thrombin" as used herein encompasses any naturally-occurring form of thrombin, including α-thrombin, β-thrombin, δ-thrombin, ε-thrombin, γ-thrombin, meizothrombin, and naturally-occurring thrombin mutants (e.g., Thrombin Quick I, Thrombin Quick II, and Prothrombin Tokishima).

The terms "heparin cofactor II" and "HCII" as used herein refer to HCII proteins from any species of origin. Preferred are mammalian HCIIs, including but not limited to, human, bovine, ovine, porcine, simian, rat and mouse HCIIs. Human HCIIs are most preferred. In addition, the terms "heparin cofactor II" and "HCII" encompass wild-type HCIIs, including naturally occurring allelic variants. Also encompassed are mutant HCIIs (i.e., in addition to the carboxyl terminal tail extension mutation) where the resulting double (or triple, quadruple, etc.) mutant has enhanced anti-thrombin activity as compared with wild-type HCII. The second (or third, fourth, etc.) mutation can be a deletion, truncation, insertion, substitution or point mutation, and a variety of HCII mutants are known in the art. See e.g., Paston and Gettins, (1994), *Thrombosis and Haemostatis* 72:166. Exemplary mutants include an HCII in which the arginine in position 103 is replaced by either a leucine, glutamine or tryptophan (Blinder and Tollefsen, (1990) *J. Biol. Chem.* 265:286), an HCII in which the arginine at position 193 is replaced by an asparagine (Ragg et al., (1990) *J. Biol. Chem.* 265:5211), an HCII in which the glutamic acid at position 69 is replaced by a glutamine and the aspartic acid at position 70 is replaced by an asparagine (Ragg et al., (1990) *J. Biol. Chem.* 265:22386), an HCII in which the tyrosine at position 73 is replaced by a phenylalanine (Id.), and $HCII_{oslo}$. Additional illustrative HCII mutants include an amino-terminally truncated HCII (Blinder et al., (1988) *Biochemistry* 27:752), as well as other truncated HCIIs.

Preferably, the claimed HCII molecules will exhibit enhanced anti-thrombin activity as compared with wild-type HCII in the absence and/or presence of polyanions and will be at least 75%, more preferably 80%, 85%, 90%, or even 95% homologous to the inventive HCII molecules disclosed herein.

Accordingly, in preferred embodiments the present invention provides compounds comprising HCII mutants with carboxyl terminal extensions that exhibit enhanced thrombin inhibitory activity. Preferred mutants comprise wild-type HCII molecules with a —$(His)_6$—COOH or —$(His)_5$Pro—COOH carboxyl terminal extension. In the most preferred embodiments, the mutant HCII has an amino acid sequence as given herein as SEQ ID NO:5 or SEQ ID NO:7 or a continuous sequence of amino acids from SEQ ID NO:5 or SEQ ID NO:7.

B. Production of HCII Mutants, Isolated DNA Encoding HCII Mutants, Vectors, and Host Cells.

The inventive HCII mutants may be produced by any means known in the art, but are preferably produced by recombinant nucleic acid techniques. Recombinant HCII can be expressed in any suitable host cell known in the art, including but not limited to, bacterial, yeast, insect, and mammalian cells by employing an appropriate expression vector. Expression vectors are well-known in the art and include, but are not limited to, bacteriophage, plasmids, yacs, baculoviruses and animal viruses. The preferred host for expression of the disclosed HCII molecules is a eukaryotic cell. Alternatively, the inventive HCII mutants can be generated by transgenic cattle, sheep, goats or pigs, etc., typically by secretion of the protein into a biological fluid (e.g., milk). See, e.g., U.S. Pat. No. 5,750,172 to Meade et al. Preferred are expression systems employing mammalian tissue culture or transgenic animals.

Expression vectors compatible with various host cells are well known in the art. Typically, an expression vector contains an "expression cassette." An "expression cassette38 according to the present invention includes, in the 5' to 3' direction, a promoter, a structural gene operatively associated with a promoter, and, optionally, a termination sequence including a stop signal for RNA polymerase and a polyadenylation signal for polyadenylase.

The term "operatively associated," as used herein, refers to DNA sequences on a single DNA molecule which are associated so that the function of one is affected by the other. Thus, a promoter is operatively associated with a structural gene when it is capable of affecting the expression of that structural gene (e.g., the structural gene is under the transcriptional control of the promoter).

Structural genes according to the present invention encode the inventive HCII mutants containing a carboxyl terminal extension, as described above. All of these regulatory regions should be capable of operating in the host cells to be transformed. The 3' termination region may be derived from the same gene as the transcriptional initiation region or may be derived from a different gene.

The present invention also provides isolated DNAs encoding the inventive HCII molecules with carboxyl terminal extensions, as defined above. The isolated DNAs encoding the inventive HCII molecules can be from any species of origin, preferably of mammalian origin, including but not limited to, human, bovine, ovine, porcine, simian, rat and mouse origin. Most preferably, the isolated DNAs are of human origin. In alternative preferred embodiments, the isolated DNAs encode the proteins given herein as SEQ ID NO:5 or SEQ ID NO:7, or a continuous amino acid sequence of SEQ ID NO:5 or SEQ ID NO:7. Such DNA sequences include those given as SEQ ID NO:4, SEQ ID NO:6, and DNA sequences derived therefrom due to the degeneracy of the genetic code.

Isolated DNAs according to the present invention also encompass DNA molecules that encode the inventive HCII molecules and are substantially homologous to the DNA sequences encoding the inventive HCII molecules disclosed herein, and particularly the isolated DNAs of SEQ ID NO:4 or SEQ ID NO:6 or continuous nucleotide sequences located therein. This definition is intended to include natural allelic variations in the DNA sequences encoding the inventive HCII molecules. As used herein, regions that are "substantially homologous" are at least 75%, and more preferably are 80%, 85% 90%, or even 95% homologous.

Isolated DNAs from other species include those which are at least about 75% homologous (an more preferably are about 80%, 85%, 90%, or even 95% homologous) to the human DNAs disclosed herein, in particular, the isolated DNAs having the sequence given herein as SEQ ID NO:4 or SEQ ID NO:6, or a continuous nucleotide sequences located therein, and which encode the inventive HCII molecules.

High stringency hybridization conditions which will permit homologous DNA sequences to hybridize to a DNA sequence as given herein are well known in the art. For example, hybridization of such sequences to DNA disclosed herein may be carried out in 25% formamide, 5×SSC, 5×Denhardt's solution, with 100 µg/ml of single-stranded DNA and 5% dextran sulfate at 42° C., with wash conditions of 25% formamide, 5×SSC, 0.1% SDS at 42° C. for 15 minutes, to allow hybridization of sequences of about 60% homology. More stringent conditions are represented by a wash stringency of 0.3 M NaCl, 0.03 M sodium citrate, 0.1% SDS at 60° C. or even 70° C. using a standard hybridization assay (see Sambrook et al., Molecular Cloning, A laboratory Manual (2d ed. 1989)). In general, DNA sequences which encode the inventive HCII molecules and which hybridize to the DNAs encoding the inventive HCII molecules disclosed here will be at least 75%, 80%, 85%, 90%, or even 95% homologous or more with the isolated DNAs disclosed herein.

C. Methods of Use of HCII Mutants.

Heparin cofactor II modulates (i.e., regulates) thrombin activity. Thrombin is a serine protease that plays a central role in the blood coagulation cascade. The present invention provides methods of administering the disclosed HCII mutants containing carboxyl terminal extensions to a subject so as to inhibit blood coagulation. The terms "inhibit" and "inhibiting," as used herein, mean halting or decreasing the extent of blood coagulation. By "halting or decreasing the extent of blood coagulation," it is intended that the HCII mutants are employed in prophylactic methods to reduce the degree of blood clot formation as compared with that observed without administration of the inventive HCII mutants. Thus, it is not necessary that administration of the HCII mutants completely prevent or eliminate blood coagulation, only that it reduces the degree of blood coagulation as compared with that observed in he absence of administration of the HCII mutants.

The inventive HCII mutants containing a carboxyl terminal extension may have enhanced anti-coagulant activity as compared with wild-type HCII. By "enhanced anti-coagulant activity," it is meant that the inventive HCII mutants inhibit blood coagulation to a greater extent than does wild-type HCII in the absence and/or presence of polyanions, such as glycosaminoglycans (e.g., heparin, heparan sulfate, dermatan sulfate, etc.).

The inventive HCII mutants may be advantageously administered to a subject in vivo to inhibit blood coagulation in a subject afflicted with or at risk for developing blood clots. Alternatively stated, the present methods can be used to treat any condition for which anti-thrombotic therapy is indicated, particularly coronary artery and cerebrovascular disease. Illustrative examples of clinical settings in which the compositions of the present invention can be used include treatment of myocardial infarction, pulmonary embolism, cerebrovascular disease, and the like. For example, they can be used in the treatment of venous thrombosis and thromboembolic disease, arterial thrombosis and thromboembolic disease, myocardial infarctions, pulmonary embolism, cerebrovascular disease, thrombotic occlusions during and subsequent to thrombolytic therapy or angioplastic therapy and, in general, any other condition for which anti-coagulant therapy is indicated. Such other conditions include primary and secondary hypercoagulable states (Nachman et al., (1993) *Ann. Intern. Med.* 119:819), including ATIII and HCII-deficient states (or other serpin deficiencies), and thrombotic complications of other diseases, for example, cancer, tumor metastasis, diabetes, chronic inflammation, sepsis, shock, Disseminated Intravascular Coagulation (DIC), and other conditions where prophylactic anti-coagulant effects are desired.

The above-described methods can also be employed in vitro to inhibit coagulation of whole blood and blood plasma, e.g., for storage or laboratory analysis. Furthermore, the present invention is useful to inhibit blood coagulation in any other medium or biological fluid in which blood coagulation is undesirable.

Thrombin is not only involved in primary hemostasis, but also the processes of wound healing (i.e., remodeling, returning the injured site essentially to a state of normalcy) and tissue repair (i.e., generation of a substantial collagen scar to fill in the gap of the injury, but not a return to normal). Following tissue injury, tissue factor (also called thromboplastin) is produced by the damaged tissue, and the released tissue factor initiates a cascade which results in the conversion of prothrombin into thrombin. The function of thrombin in this situation appears to be related to the inflammatory/immune responses that develop following injury. See U.S. Pat. No. 5,583,102 to Lentz et al.

In addition to its serine protease activity, thrombin is a chemotactic and/or mitogenic factor for monocytes, vascular smooth muscle cells, and fibroblasts. There is also evidence that thrombin promotes angiogenesis (by stimulating vascular endothelial cell proliferation), granulation tissue formation (by stimulating macrophages and fibroblasts), and re-epithelialization (by activating basal layer keratinocytes). U.S. Pat. No. 5,583,102 to Lentz et al. Through its chemotactic properties, thrombin is implicated in the host response to injury (e.g., wound healing and tissue repair).

Heparin cofactor II is believed to inhibit the chemotactic and mitogenic activities of thrombin, in addition to thrombin-induced coagulation. Church and Hoffman, (1994) *TCM* 4:140. It has previously been demonstrated that HCII blocks thrombin-induced monocyte chemotaxis. Hoffman et al., (1990) *J. Leukoc. Biol.* 48:156. Accordingly, the present invention also provides methods of modulating (i.e., regulating or controlling) wound healing and tissue repair in a subject by administering the mutant HCII molecules containing a carboxyl terminal extension to a subject in need thereof. The inventive HCII mutants can be administered to regulate wound healing and tissue repair processes by modulating (i.e., regulating or controlling, for example, inhibiting) the inflammatory and immunostimulatory activities (i.e., cytokine-like actions) of thrombin following injury. By the expressions "regulate wound healing" and "regulating wound healing," it is meant that the inventive HCII mutants can be administered to promote healing of wounds. While not wishing to be limited by any particular theory of the invention, typically the HCII mutants will not be administered so as to interfere with the normal (i.e., physiological) actions of thrombin following injury, but only pathological actions, such as in persistent and chronic wounds. Likewise, by the expressions "regulate tissue repair" and "regulating tissue repair," it is meant that the inventive HCII mutants can be administered to promote repair of chronic or persistent tissue injury. By "promote healing" or "promote repair" it is meant that the inventive HCII mutants stimulate or enhance wound healing or tissue repair to a greater extent than does wild-type HCII in the absence and/or presence of polyanions, such as glycosaminoglycans (e.g., heparin, heparan sulfate, dermatan sulfate, etc.).

Wounds are internal or external bodily injuries or lesions caused by physical means, such as mechanical, chemical, bacterial, or thermal (e.g., burn wounds) means, which disrupt the normal continuity of structures. Such bodily injuries include contusions, wounds in which the skin is unbroken, incisions, wounds in which the skin is broken by a dull or blunt instrument, wounds caused by accidents, and wounds caused by surgical procedures. Sites of wound healing and/or tissue repair can be both cutaneous and non-cutaneous. The present invention can be advantageously, and preferably, employed to promote healing of chronic wounds such as chronic leg ulcers in diabetic patients, bed sores, chemotherapy induced wounds, and for treatment of skin diseases caused by thrombin over-stimulation (associated with dysfunctional regulation of fibroblast or keratinocytes) including, but not limited to, psoriasis, hyperkeratosis, lichen planus, scleroderma, morphea, lichen sclerosis et atrophica, and to enhance healing of non cutaneous wounds such as oral ulcers, vaginal ulcers, esophageal ulcers, and other ulcers of the gastrointestinal, urinary or reproductive tracts. Alternatively, the disclosed HCII mutants can be administered to promote repair or healing of atherosclerotic lesions. As a further alternative, administration of the inventive compositions and pharmaceutical formulations can be used to control excessive scar tissue formation or chronic ulceration.

As a further aspect of the present invention, HCII can be advantageously administered to inhibit inflammation (i.e., prevent or reverse inflammation) in a subject in need thereof. The terms "inhibit" or "inhibiting," as used herein include both the concepts of preventing inflammation as well as alleviating inflammation. Furthermore, by "inhibit" or "inhibiting" it is intended that administration of the inventive HCII mutants reduces or alleviates inflammation as compared with the degree of inflammation observed in the absence of the inventive HCII mutants. By the expression "enhanced anti-inflammatory activity," it is meant that the disclosed HCII mutants have greater anti-inflammatory effects than does wild-type HCII in the absence and/or presence of polyanions, such as glycosaminoglycans (e.g., heparin, heparan sulfate, dermatan sulfate, etc.).

The inventive HCII mutants can be administered to any subject afflicted with or at risk for inflammation or inflammatory disease. For example, HCII mutants of the present invention can be administered to inhibit inflammation following injury, wounding, tissue damage, or surgery. In addition, the inventive methods can be employed to inhibit inflammation in subjects afflicted with or at risk for septicemia, Disseminated Intravascular Coagulation (DIC), and arthritis.

Furthermore, in all of the above-described methods, the HCII mutants of the present invention are effective in inhibiting both the intravascular and extravascular effects of thrombin. See Church and Hoffman, (1994) *TCM* 4:140. Thrombin is implicated in thrombosis within intact vessels, which results in a pathological intravascular coagulation. There is evidence, however, that the normal function of HCII is as an extravascular thrombin inhibitor. Id. Thrombin-mediated hemostasis occurs extravascularly following rupture of the vascular wall, which is the postulated site of HCII action. The HCII mutants, pharmaceutical formulations, and methods disclosed herein can be employed to inhibit both the intra- and extra-vascular aspects of thrombin action.

D. Subjects, Dosages, Pharmaceutical Formulations, and Routes of Administration.

The methods of the present invention are useful in vivo for medical or veterinary treatment of any subject in need of the anti-thrombin actions of the disclosed HCII mutants. Any animal subject is suitable, with mammals (e.g., humans, horses, cattle, sheep, goats, pigs, dogs and cats) and avians (e.g., chickens, ducks, turkeys, parrots) being preferred. Mammalian subjects are more preferred, with human subjects being the most preferred.

The HCII mutants are employed in vitro or in vivo in an amount effective to give the desired thrombin inhibitory effects. When administered in vivo, the HCII compositions disclosed herein may be administered alone or as part of a pharmaceutical formulation, as described below. Likewise, when employed in vitro, HCII may be used alone or in conjunction with other agents.

By an "effective" amount of the disclosed HCII mutants to give a particular result, it is meant that a quantity of the inventive HCII mutants (or a pharmaceutically acceptable salt or salts thereof) sufficient to accomplish the intended treatment is administered. The precise amount of the HCII mutant to be administered is not critical and may be determined in a routine manner. The dosage will vary depending on the age and species of the subject, the desired effect, the particular mutant administered, and the route of administration. Preferred dosages may be determined by simply administering a composition containing a known amount of a particular HCII mutant in vitro or in vivo to a subject, and monitoring the sample or subject for the desired effect. Techniques for formulation and administration of the compounds of the instant application may be found in Remington's "Pharmaceutical Sciences", Mack Publishing Co., Easton, Pa., latest edition.

There are no particular upper or lower limits to the dosage of HCII mutants to be administered according to the present invention. For in vivo administration, dosages can be as low as 10, 3.0,1.0, 0.5, 0.1, 0.01, or 0.001 $\mu$g/kg body weight, or less. In vivo dosages can be as high as 10, 30, 50, 100, 250, 500, 1000, 5000, 10000 or 50000 $\mu$g/kg body weight, or more.

Similarly, there are no particular upper or lower limits to the concentration of the claimed complexes to be administered in vitro. For in vitro administration, concentrations can be as low as 10, 5, 1, 0.5, 0.1, 0.01, or 0.001 ng/ml of medium, or less. In vitro concentrations can be as high as 10, 50, 100, 500, 1000, 5000, 10000 or 50000 ng/ml of medium or more.

In preferred embodiments of the above-described methods, the disclosed HCII mutants are co-administered with a polyanion (e.g., a glycosaminoglycan). It is known to those skilled in the art that polyanions accelerate the thrombin inhibitory actions of HCII. Heparin cofactor II mutants are known which possess decreased polyanion cofactor requirements. Derechin et al., (1990) *J. Biol. Chem.* 265:5623; U.S. Pat. Nos. 5,118,793 and 5,102,995 to Tollefsen et al. Exemplary polyanions include but are not limited to heparin (including low molecular weight heparin), heparan sulfate, dermatan sulfate (including low molecular weight dermatan sulfate), chondroitin sulfate E, chondroitin polysulfate 1, chondroitin polysulfate 5, hyaluronic acid, pentosan polysulfate, dextran sulfate, fucoidan, phosvitin, polyphosphate, polycarboxylates, polysulfates, polyaspartate, polyglutamate, mellitic acid, polyvinyl sulfate, polyadenylate, and polyguanylate. Preferred polyanions are glycosaminoglycans, more preferred are heparin, heparan sulfate, dextran sulfate, and dermatan sulfate, with heparin and heparan sulfate being most preferred.

By "co-administered," the HCII mutant and polyanion may be administered together in a pharmaceutical formulation, as described in more detail below. Alternatively, the HCII mutant and polyanion may be concurrently administered as separate compounds. By "co-administered" or "concurrently administered" it is meant that the HCII mutant and polyanion are administered during the same course of treatment, typically within minutes of one another, not necessarily at the same exact moment.

The precise amount of polyanion cofactor to be administered is not essential and can be routinely determined using methods known in the art. Typically, a dosage will be chosen to optimally enhance the anti-thrombin activities of the HCII mutants disclosed herein. In general, the precise dosage will vary with the particular polyanion, the particular HCII mutant, the desired effect, the condition of the subject, and the route of administration.

While not wishing to be held to any particular theory of the invention, the prevalent view in the art is that polyanions accelerate the rate of HCII inhibition of thrombin by a "template" or "bridging" mechanism. See e.g., Pratt and Church, (1993) *Blood Coag. and Fibrinol.* 4:479; Pratt et al., (1992) *J. Biol. Chem.* 265:8795. According to this model, polyanions act as a template or bridge that bind both HCII and thrombin. Thus, at low polyanion concentrations the reactants are brought into close proximity, thereby catalyzing the inhibition reaction. At high polyanion concentrations, on the other hand, it is believed that the polyanion interacts with individual inhibitor or thrombin molecules, which results in the sequestration of the individual reactants and a slowing down of the inhibition reaction. This model is in accord with the observation that the concentration-dependence curves for thrombin inhibition by HCII in the presence of polyanions are bell-shaped. Thus, according to the present invention, optimal concentrations of polyanion will be sufficient to catalyze the inhibition reaction, but insufficient to reach the downward sloping portion of the concentration-dependence curve.

There is also evidence that polyanions accelerate HCII inhibition of thrombin through an allosteric mechanism. Sheehan et al., (1994) *J. Biol. Chem.* 269:32747. The allosteric model posits an interaction between HCII and glycosaminoglycan, independent of thrombin, which results in activation of HCII anti-thrombin activity. Thus, the inventive HCII mutants and polyanion cofactor can be incubated together, in the absence of thrombin, so as to activate the HCII molecules prior to administration.

In general, the inventive HCII mutants disclosed herein have increased affinity for heparin and heparan sulfate, which shifts the concentration-dependence curve of thrombin inhibition to the left. Accordingly, optimal concentrations for heparin or heparan sulfate cofactor will be diminished as compared with wild-type HCII, preferably, at least a 25%, 40%, 50%, 70%, 80% or more reduction in the concentration of heparin or heparan sulfate required for mutant HCII molecules as compared with wild-type HCII.

The HCII mutants containing carboxyl terminal extensions may be administered to a subject alone or in a pharmaceutical formulation where it is mixed with other active agents or cofactors in a pharmaceutically acceptable carrier or excipient(s). As described above, the HCII mutants of the present invention can be administered in conjunction with a polyanion cofactor. In addition, compositions comprising HCII mutants can be administered in conjunction with other active agents, such as anti-coagulants, pro-fibrinolytic agents (e.g., urokinase, streptokinase, or tissue plasminogen activator), antibiotics, or anti-inflammatory agents. The anticoagulant compositions of the present invention can be administered along with conventional compositions used in the art.

Suitable routes of administration may, for example, include oral, rectal, transmucosal, topical or intestinal administration; parenteral delivery, including intramuscular, subcutaneous, intramedullary injections, as well as intrathecal, direct intraventricular, intravenous, intraperitoneal, intranasal, or intraocular injections. Alternately, one may administer the compound in a local rather than systemic manner, for example, in a depot or sustained release formulation. Parenteral, topical and intestinal routes of administration are preferred. When administered in a pharmaceutical formulation with polyanion (e.g., heparin), intravenous and intramuscular injection are preferred.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes. Pharmaceutical compositions for use in accordance with the present invention thus may be formulated in a conventional manner using one or more pharmaceutically acceptable carriers comprising excipients and auxiliaries that facilitate processing of the active compounds into preparations which can be used pharmaceutically. Proper formulation is dependent upon the route of administration chosen.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained from a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as the cross-linked polyvinyl pyrrolidone, agar, or algiic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichiorodifluoromethane, trichiorofluoromethane, dichiorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. Administration by inhalation may also include inhalation of dry aerosols.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. Certain organic solvents such as DMSO also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For topical administration, salves, gels, creams, ointments, lotions, foams and sprays are particularly useful.

Additionally, the disclosed pharmaceutical formulations may be administered on solid supports, including bandages and applicators which are impregnated with the mutant HCII molecules.

The compositions may, if desired, be presented in a pack or dispenser device which may contain one or more unit dosage forms containing the active ingredient or other compounds to be administered in combination with the composition. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of diseases and disorders by inhibition of thrombin activity.

The following Examples are provided to illustrate the present invention, and should not be construed as limiting thereof.

EXAMPLE 1

Materials and Reagents

Bovine serum albumin (BSA), carboxypeptidase A (CPA), and the substrate succinyl-Ala-Ala-Pro-Phe-p-nitroanilide were obtained from Sigma (St. Louis, Mo.). Tosyl-Gly-Pro-Arg-p-nitroanilide (Chromozym TH) and methoxycarbonyl cyclohexylglycyl-Gly-Arg-p-nitroanilide (Spectrozyme FXa) were obtained from Boehringer Mannheim (Indianapolis, Ind.) and American Diagnostica (Greenwich, Conn.), respectively. Restriction enzymes were obtained from either New England Biolaboratories (Beverly, Mass.) or Boehringer Mannheim (Indianapolis, Ind.). Heparin-Sepharose was from Pharmacia (Piscataway, N.J.) and Q-Sepharose was from Sigma. Human antithrombin III deficient plasma (catalog #203) and normal hemostasis reference plasma (catalog #258N) were purchased from American Diagnostica, (Greenwich, Conn.). Human ATIII cDNA (#57224) was obtained from ATCC (Rockville, Md.). Heparin was obtained from Diosynth (The Netherlands) and dermatan sulfate was purchased from Calbiochem (La Jolla, Calif.) and nitrous acid treated to remove contaminating heparin and heparan sulfate (Teien, A. N., Abildgaard, U., and Hook, M. (1976) *Thromb. Res.* 8, 859–867). Goat anti-mouse IgG-alkaline phosphatase conjugate, goat anti-mouse IgG-horseradish peroxidase conjugate, and goat anti-rabbit IgG-alkaline phosphatase conjugate were purchased from SigmaImmuno Chemical. Rabbit antihuman anti-thrombin III antibody was purchased from Dako Corp. (Carpinteria, Calif.). Monoclonal antibody 2-4-34 to purified human plasma HCII was made in our laboratory using standard techniques. Human α-thrombin, HCII, and ATIII were purified in our laboratory from plasma as described previously (Griffith, M. J., Noyes, C. M., Tyndall, J. A., and Church, F. C. (1985) *Biochemistry* 24, 6777–6782; Church, F. C., and Whinna, H. C. (1986) *Anal. Biochem.* 157, 77–83). An $N^{\alpha}$-acetylated-hexahistidine synthetic peptide was synthesized and purified by Professor David G. Klapper (Department of Microbiology & Immunology, UNC-CH School of Medicine).

EXAMPLE 2

Mutagenesis and Expression of Recombinant Proteins

Human wild type recombinant HCII (cDNA kindly provided by Dr. Douglas M. Tollefsen, Washington University School of Medicine, St. Louis, Mo.) was previously expressed in the baculovirus expression system and characterized (Ciaccia, A. V., Cunningham, E. L., and Church, F. C. (1995) *Protein Express. Purific.* 6, 806–812). To facilitate our studies of HCII, site-directed mutagenesis (Kunkel, T. A., Roberts, J. D., and Zakour, R. A. (1987) *Meth. Enzymol.* 154, 367–382) was performed on full-length HCII cDNA subcloned into the pBlueScript SK+ mutagenesis and cloning vector (Stratagene, La Jolla, Calif.) (Ciaccia, A. V., Willemze, A. J., and Church, F. C. (1997) *J. Biol. Chem.* 272(2), 888–893) at two sites to encode the identical amino acid sequence but it contains two nucleotide changes (at base pairs 595 and 1255) that create unique restriction sites (NheI and AflII) in the cDNA. DNA sequencing using a Sequenase Version 2.0 kit (Amersham, Cleveland, Ohio) identified positive clones. Full-length HCII cDNA containing these unique restriction sites was then subcloned into the baculoviral transfer vector pVL1392 (PharMingen, La Jolla, Calif.) via flanking EcoRI sites as described previously (Ciaccia, A. V., Willemze, A. J., and Church, F. C. (1997) *J. Biol. Chem.* 272(2), 888–893).

Using this new HCII cDNA, a cassette of the cDNA was then subcloned into pBlueScript SK+ with XhoI and EcoRI. This cassette was then used to prepare rHCII-CHis$_6$, rHCII-L444R, and rHCII-L444R-CHis$_6$ by Kunkel's method of oligonucleotide-directed mutagenesis using the primers 5'-GCCAACCCCAGCAGGTCC(CAC)$_6$TAGAGGTGGAGGTCTAGG-3' (SEQ ID NO:1), 5'-GGGGTTCATGCCGCGGTCCACCCAAGTCCG-3' (SEQ ID NO:2), or both, respectively (Kunkel, T. A., Roberts, J. D., and Zakour, R. A. (1987) *Meth. Enzymol.* 154, 367–382). DNA sequencing using Sequenase identified positive clones. Cassettes containing the mutations were then excised with AflII and XbaI and subcloned into pVL1392 containing the full-length HCII cDNA cut with the same restriction enzymes.

A full-length human ATIII cDNA was obtained from ATCC (catalog #57224) in the vector pKT218. The ATIII-containing vector was digested with PstI and this insert contained 1.6 kB of open reading frame including the signal peptide sequence, and was subcloned into the baculoviral transfer vector pVL1392 cut with the same restriction enzyme.

Using this wt-ATIII cDNA, a cassette of the cDNA was subcloned into pBlueScript SK+ with SacI and XbaI. This construct was then mutated (Kunkel, T. A., Roberts, J. D., and Zakour, R. A. (1987) *Meth. Enzymol.* 154, 367–382) to form rATIII-cassette-CHis$_6$ with the primer 5'-GGTGCAAAGAATAAGAACATTTTA(GTG)$_6$CTTAACACAAGGGTTGGC3' (SEQ ID NO:3). DNA sequencing using Sequenase identified positive clones. The mutated cassette was excised from pBlueScript with the restriction enzymes NcoI and XbaI and subcloned into pVL1392 containing the full-length ATIII gene cut using the same restriction enzymes.

HCII and ATIII-containing pVL1392 constructs were co-transfected with linearized *Autographica californica* nuclear polyhedrosis virus into *Spodoptera frugiperda* (Sf9) insect cells (Invitrogen, Carlsbad, Calif.) in T25 flasks using BaculoGold Baculovirus Transfection Kits (Pharmingen, La Jolla, Calif.) as detailed previously (Ciaccia, A. V., Cunningham, E. L., and Church, F. C. (1995) *Protein Express. Purific.* 6, 806–812; Ciaccia, A. V., Willemze, A. J., and Church, F. C. (1997) *J. Biol. Chem.* 272(2), 888–893). Media was collected from these cells five days post-transfection as recombinant viral stock. Production of rHCII (wt, CHis$_6$, CHis$_5$Pro, L444R, or L444R-CHis$_6$) or rATIII (wt or CHis$_6$) was verified by immunoblot analysis of whole cell lysates. Recombinant viral stocks were amplified and stored at −80° C. Sf9 cells were maintained in Grace's medium supplemented with 10% fetal bovine serum, 0.3 g/L L-glutamine, and 50 µg/mL gentamicin.

EXAMPLE 3

Protein Expression and Purification

Expression of both rHCII and rATIII was performed using HighFive™ insect cells (Invitrogen, Carlsbad, Calif.) maintained at 27° C. in Excel 405 medium (JRH Biosciences, Lenexa, Kans.). Recombinant HCII proteins were purified by sequential heparin-Sepharose and Q-Sepharose chromatography steps as described previously (Ciaccia, A. V., Cunningham, E. L., and Church, F. C. (1995) *Protein Express. Purific.* 6, 806–812; Ciaccia, A. V., Willemze, A. J., and Church, F. C. (1997) *J. Biol. Chem.* 272(2), 888–893). The final rHCII eluates were dialyzed into HNPN at pH 7.4 and stored at −20° C.

The preparation and purification of the rATIII proteins began by infecting four T150 flasks of sub-confluent High-Five™ cells on day one with specific recombinant viral stocks. Two to three days post-infection, media was decanted from cells and cell debris was spun out by centrifugation at 350×g for 10 min in a Centra-8 centrifuge (International Equipment Co., Needham Heights, Mass.). The cleared media (~100 mL) was diluted with an equal volume of a buffer made up of 20 mM Hepes, pH 6.5, 0.2% PEG, and 0.02% NaN$_3$. One mL of a 1:1 slurry of heparin-Sepharose in HNPN buffer (20 mM Hepes, pH 7.4, 150 mM NaCl, 0.1% PEG, 0.05% NaN$_3$) was added to the diluted media and tumbled at 42° C. for 1 hr. Heparin-Sepharose beads were then pelleted at 50×g for 5 min and washed two times with 750 mM NaCl. The protein was eluted off of heparin-Sepharose with 20 mM Hepes, pH 7.4, 2.0 M NaCl 0.1 % PEG, and 0.02% NaN$_3$. The final eluate was dialyzed into HNPN at pH 7.4 and stored at −20° C. In all experiments wild-type recombinant proteins were compared to their plasma purified counterparts and found to be essentially equivalent.

Concentrations of rHCII and rATIII were determined by enzyme linked immunosorbent assay (ELISA) using purified plasma proteins as the standard. Immunoblot analysis was carried out using a Phast System (Pharmacia, Piscataway, N.J.) (Ciaccia, A. V., Cunningham, E. L., and Church, F. C. (1995) *Protein Express. Purific.* 6, 806–812; Ciaccia, A. V., Willemze, A. J., and Church, F. C. (1997) *J. Biol. Chem.* 272(2), 888–893).

EXAMPLE 4

Protease Inhibition

Protease inhibition rates were determined as described previously (Rogers, S. J., Pratt, C. W., Whinna, H. C., and Church, F. C. (1992) *J. Biol. Chem.* 267(6), 3613–3617; Whinna, H. C., Choi, H. U., Rosenberg, L. C., and Church, F. C. (1993) *J. Biol. Chem.* 268, 3920–3924; Ciaccia, A. V., Cunningham, E. L., and Church, F. C. (1995) *Protein Express. Purific.* 6, 806–812; Ciaccia, A. V., Willemze, A. J., and Church, F. C. (1997) *J. Biol. Chem.* 272(2), 888–893). All assays were performed at room temperature in 96-well microtiter plates previously coated with 2 mg/mL BSA.

In the absence of glycosaminoglycan, 50–100 nM rHCII (wt, CHis$_6$, CHis$_5$Pro, L444R, or L444R-CHis$_6$) or rATIII (wt or CHis$_6$) was incubated with 1 nM thrombin, 0.5 nM Factor Xa, 2 nM chymotrypsin, or 5 nM trypsin, in the presence of 1 mg/mL Polybrene (pB) (for thrombin and Factor Xa) and 2 mg/mL BSA in HNPN, pH 7.4.

In the absence of glycosaminoglycan with either hirugen (synthetic peptide based on the carboxyl-terminal region of the protein hirudin from residues 53–64) or a control peptide corresponding to the reverse sequence of the HCII acidic domain (residues 47–61) at 20 μM, rHCII (wt at 200 nM, CHis$_6$ at 100 nM, and L444R or L444R-CHis$_6$ at 50 nM) was incubated with 1 nM thrombin in the presence of 1 mg/mL pB and 2 mg/mL BSA in HNPN, pH 7.4 (Ciaccia, A. V., Monroe, D. M., and Church, F. C. (1997) *J. Biol. Chem.* 272(22), 14074–14079).

In the presence of glycosaminoglycans, 5 nM rHCII (wt, CHis$_6$, CHis$_5$Pro, L444R, or L444R-CHis$_6$) was incubated with 0.5 nM thrombin and 0–1 mg/mL heparin or 0–4 mg/mL dermatan sulfate or 10 nM rATIII (wt or CHis$_6$) was incubated with 1 nM thrombin or factor Xa and 0–1 mg/mL heparin in the presence of 2 mg/mL BSA in HNPN, pH 7.4.

Residual thrombin activity was measured with 150 μM GlyProArg-NA and 1 mg/mL pB in the absence of glycosaminoglycan, 2 mg/mL pB in the presence of heparin and 4 mg/mL in the presence of dermatan sulfate. Residual factor Xa activity was measured with 500 μM Spectrozyme FXa and 2mg/mL pB in the presence or absence of glycosaminoglycan. Residual chymotrypsin activity was measured with 150 μM AlaAlaProPhe-NA and residual trypsin activity was measured with 150 μM GlyProArg-NA. Substrate cleavage was measured by color development at 405 nM on a V$_{max}$ Kinetic Microplate Reader (Molecular Devices).

Assays were performed at least in triplicate on two or more recombinant protein preparations. All inhibition studies were measured under pseudo-first order conditions where inhibitor [I] is at least ten-fold higher than enzyme (protease) [E], and second-order rate constants were calculated as described previously (Ciaccia, A. V., Cunningham, E. L., and Church, F. C. (1995) *Protein Express. Purific.* 6, 806–812; Ciaccia, A. V., Willemze, A. J., and Church, F. C. (1997) *J. Biol. Chem.* 272(2), 888–893).

EXAMPLE 5

Heparin-Sepharose Affinity Chromatography

To determine relative heparin affinities, 3–6 μg of rHCII protein was diluted in 20 mM Hepes, pH 7.4, and was run on a 1-mL heparin-Sepharose column (equilibrated in 20 mM Hepes, pH 7.4, and 50 mM NaCl) using an FPLC® System (Pharmacia, Piscataway, N.J.). After the samples were loaded on the column, the proteins were eluted with a 40 mL gradient of 20 mM Hepes, pH 7.4, from 50–800 mM NaCl and 1 mL fractions were collected. 100 μL of each fraction was aliquoted onto a 96-well microtiter plate and ELISA was performed. The peak elution ionic strength was determined by plotting 405 nm color development and NaCl concentration against the fraction number. All samples were run at least in triplicate using two or more protein preparations. Recombinant ATIII samples were run similarly to the HCII samples, except the elution gradient was run from 50 mM to 2 M NaCl.

EXAMPLE 6

Carboxypeptidase A Treatment

Carboxypeptidase A (CPA) stored in toluene was washed with dH$_2$O and then dialyzed into HNPN buffer at pH 7.4. Forty ng of CPA was combined with approximately 1 μg of recombinant protein and incubated at room temperature. Following a 2-hr incubation at room temperature, 2 mM EDTA was added to quench CPA activity. Controls were run in which EDTA was added to the reaction prior to the addition of CPA. CPA digested proteins were then assayed according to previously mentioned procedures.

EXAMPLE 7

Plasma Assays

The assay to evaluate rHCII (wt and rHCII-CHis$_6$) in plasma was designed based on previously published methods (Tollefsen, D. M., and Pestka, C. A. (1985) *Blood* 66(4), 769–774; Griffith, M. J., Carraway, T., White, G. C., and Dombrose, F. A. (1983) *Blood* 61(1), 111–118). All assays were performed at room temperature in 96-well microtiter plates previously coated with 2 mg/mL BSA. This assay was performed using normal hemostasis reference plasma (REF), human antithrombin III-deficient plasma (DEF), or a 50:50 mixture of these plasmas (REF/DEF). Within the assay, 10 nM rHCII or rHCII-CHis$_6$ was incubated for 15 sec with I nM thrombin and 1 μg/mL heparin or 50 μg/mL dermatan sulfate, in the presence of a 1:100 dilution of plasma. Residual thrombin activity was measured with 300 μM GPA and 2 mg/mL pB. Substrate cleavage was measured by color development at 405 nM on a V$_{max}$ Kinetic Microplate Reader. Second order rate constants were measured at least in triplicate on two recombinant protein preparations as described in Example 4.

EXAMPLE 8

Inhibition of Thrombin by rHCII-CHis$_6$ in the Absence of Glycosaminoglycan

Recombinant HCII proteins were generated using Kunkel's method of oligonucleotide directed mutagenesis as described in Example 2. More specifically, rHCII-CHis$_6$ was made by inserting six histidine codons directly before the TAG stop codon (FIG. 1; SEQ ID NO:4 and SEQ ID NO:5). Using a baculoviral expression system, we typically obtained ~60 μg of protein from four T1 50 flasks of HighFive™ cells infected with recombinant viral stock. After purification, immunoblot analysis showed that rHCII-CHis$_6$ was a single band that co-migrated with wt-rHCII.

Heparin cofactor II inhibits two serine proteases, thrombin and chymotrypsin. We have compared the rates of inhibition of these proteases by rHCII-CHis$_6$ and wt-rHCII (Table I). In the absence of glycosaminoglycan, the rate of thrombin inhibition by rHCII-CHis$_6$ is significantly faster (1.5-fold) than that of wt-rHCII. However, when comparing the same proteins in their ability to inhibit chymotrypsin, we see that wt-rHCII and rHCII-CHis$_6$ are essentially the same.

TABLE I

HCII and ATIII Inhibition of
Serine Proteases in the Absence of Glycosaminoglycan[a]

| Protease | Serpin | k$_2$ × 10$^4$(M$^{-1}$min$^{-1}$)[b] | Ratio (mutant/wt serpin) |
|---|---|---|---|
| Thrombin | wt-rHCII | 1.30 ± .19 | — |
|  | rHCII-CHis$_6$ | 1.92 ± .10[c] | 1.48 |
|  | wt-rATIII | 10.4 ± 2.3 | — |
|  | rAT-ATIII-CHis$_6$ | 8.81 ± 1.3[d] | .847 |
| Factor Xa | wt-rATIII | 16.4 ± 1.2 | — |
|  | rAT-ATIII-CHis$_6$ | 9.87 ± .57[e] | .617 |
| Chymotrypsin | wt-rHCII | 71.0 ± 12 | — |
|  | rHCII-CHis$_6$ | 61.0 ± 16[f] | .860 |

TABLE I-continued

HCII and ATIII Inhibition of
Serine Proteases in the Absence of Glycosaminoglycan[a]

| Protease | Serpin | $k_2 \times 10^4 (M^{-1} min^{-1})$[b] | Ratio (mutant/wt serpin) |
|---|---|---|---|
| Trypsin | wt-rATIII | 184 ± 57 | — |
|  | rATIII-CHis$_6$ | 180 ± 91[d] | .978 |

[a]Inhibition of proteases by rHCII and rATIII mutants was measured in the absence of glycosaminoglycans. Values are expressed as means ± S.D. The statistical significance of the data was evaluated using Student's t-tests; P-values >0.05 were considered significant.
[b]Rate constants are the mean values of 3–9 separate determinations with at least 3 different preparations of recombinant protein.
[c]p≦0.003 compared with wt-rHCII.
[d]Not statistically different from wt-rATIII.
[e]p≦0.001 compared with wt-rATIII.
[f]Not statistically different from wt-rHCII.

EXAMPLE 9

Inhibition of Thrombin by rHCII-CHis$_6$ in the Presence of Glycosaminoglycan

Inhibition of thrombin activity by wt-rHCII and rHCII-CHis$_6$ was examined in the presence of glycosaminoglycans. The inhibition assays were carried out as described in Example 4.

CHis$_6$ with heparin is increased over 100,000-fold and is comparable to rates obtained with the physiologic thrombin inhibitor ATIII with heparin.

Figure 2B:
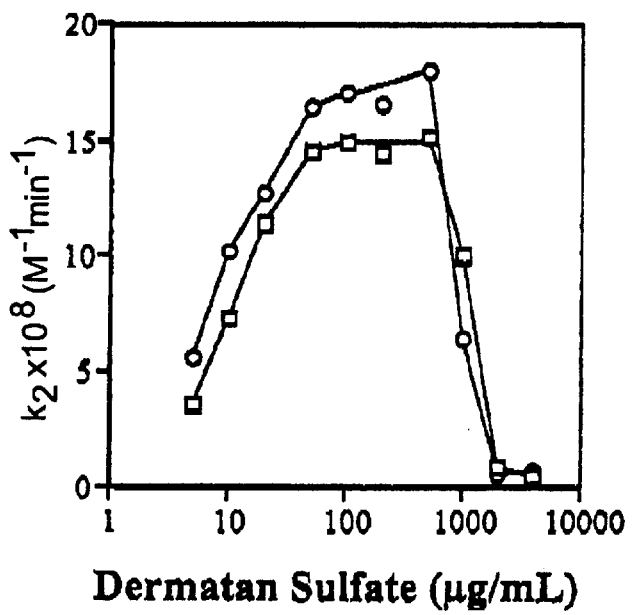

We do not see any change in rates of thrombin inhibition in the presence of the glycosaminoglycan, dermatan sulfate. As shown in the bottom panel of FIG. 2, the maximal rate of thrombin inhibition is $1.52±0.31×10^9$ $M^{-1}$ $min^{-1}$ for wt-rHCII and $1.80±0.50×10^9$ $M^{-1}$ $min^{-1}$ for rHCII-CHis$_6$ maximal inhibition is seen at approximately 500 μg/mL of dermatan sulfate for both proteins. These data, which are also summarized in Table II, indicate that the addition of the carboxyl-terminal histidine tag does not affect the rate at which thrombin inhibition by HCII is accelerated by dermatan sulfate.

EXAMPLE 10

Affinity of rHCII-CHis$_6$ for Heparin-Sepharose

We further assessed the ability of these proteins to bind heparin-Sepharose. As shown in Table II, rHCII-CHis$_6$ eluted at almost two times the NaCl concentration as wt-rHCII, 575 mM vs. 350 mM, respectively. Taken together with the enhanced heparin cofactor activity of rHCII-CHis$_6$, these data indicate that the hexahistidine tag endows HCII with increased heparin binding.

TABLE II

HCII and ATIII Inhibition of Serine Proteases in the Presence of Glycosaminoglycans[a]
Inhibition Rate[b] $k_2 \times 10^8$ $(M^{-1}min^{-1})$

| Serpin | Thrombin + heparin | Ratio (variant/wt) | Thrombin + dermatan sulfate | Ratio (variant/wt) | Factor Xa + heparin | Ratio (variant/wt) | Heparin-Sepharose [NaCl] (mM) |
|---|---|---|---|---|---|---|---|
| wt-rHCII | 9.29 ± 2.8 (50)[c] | — | 15.2 ± 3.1 (500) | — |  |  | 350 |
| rHCII-CHis$_6$ | 22.3 ± 4.3[d] (5) | 2.4 | 18.0 ± 5.0[f] (500) | 1.2 |  |  | 575 |
| wt-rATIII | 5.26 ± 68 (1) | — |  |  | 1.41 ± .39 (10) | — | 975 |
| rATIII-CHis$_6$ | 2.87 ± 54[e] (2) | .55 |  |  | .785 ± .28[e] (10) | .56 | 975 |

[a]Inhibition of serine proteases by rHCII and rATIII variants was measured in the presence of increasing concentrations of either heparin or dermatan sulfate. The maximal inhibition of each curve was used in the calculation of the average inhibition rate. Values are expressed as means ± S.D. The number in parentheses that follows indicates the average glycosaminoglycan concentration at which the maximal rate was measured. The final column indicates the peak NaCl concentration at which each variant eluted from heparin-Sepharose. The statistical significance of the data was evaluated using Student's t-test; P-values < 0.05 were considered significant.
[b]Rate constants are the mean values of 3–6 separate determinations on at least 3 different protein preparations.
[c]Values in parentheses indicate optimal heparin concentration.
[d]p ≦ 0.029 compared with wt-rHCII.
[e]p ≦ 0.020 compared with wt-rATIII.
[f]Not statistically different from wt-rHCII The antithrombin properties of HCII can be enhanced more than 10,000-fold by the addition of glycosaminoglycans such as heparin or dermatan sulfate. The carboxyl-terminal histidine-tagged HCII influences the heparin-accelerated antithrombin activity. As shown in the top panel of FIG. 2, the maximal rate of wt-rHCII inhibition of thrombin is $9.29±2.8×10^8$ $M^{-1}$ $min^{-1}$ at 50–100 μg/mL heparin. However, we see over a 2-fold increase in the rate of thrombin inhibition by rHCII-CHis$_6$ at $2.23±0.43×10^9$ $M^{-1}$ $min^{-1}$ at only 5 μg/mL heparin. Therefore, in addition to the increase in rate, we also see an approximate 20-fold decrease in the amount of heparin required for maximal activity. These results are summarized in Table II and indicate that the histidine tag augmented HCII's ability to inhibit thrombin in the presence of heparin. Addition of an N-acetylated-hexahistidine peptide at 1,000 molar excess to wt-rHCII had neither a positive or negative affect on the heparin cofactor activity of HCII (data not included). These data suggest that the rate of thrombin inhibition by rHCII-

EXAMPLE 11

Figure 3A:
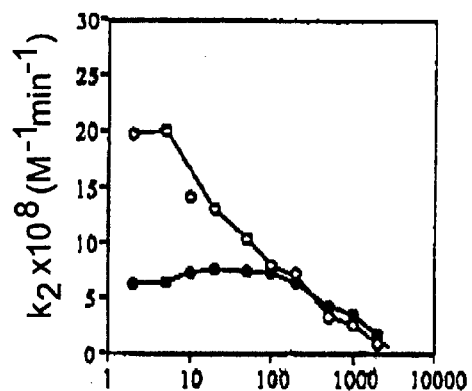
FIG. 3 is a graphical representation showing carboxypeptidase A reversibility of rHCII mutants. Thrombin inhibition assays in the presence of heparin were performed as detailed in Example 4 with plasma-purified α-thrombin and increasing amounts of heparin. The top panel shows the curves for rHCII-CHis$_6$ pre- ◯ and post- (●) CPA digest. The middle panel shows the curves for wt-rHCII pre- ❏ and post- (■) CPA digest. The bottom panel shows the curves for rHCII-CHis$_5$Pro pre- (△) and post- (▲) CPA digest. The curves shown are representative data.
Figure 3B:
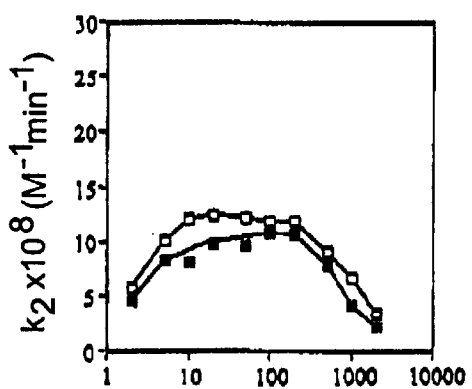
Figure 3C:
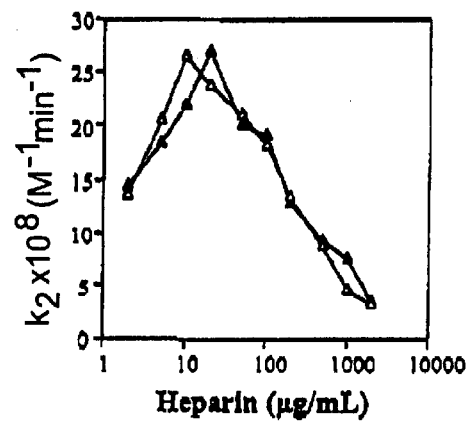

Reversal of Enhanced Activity of rHCII-CHis$_6$ by Digestion with Carboxypeptidase A To ensure that the enhanced activity of rHCII-CHis$_6$ could be attributed to the histidine tag, we attempted to remove the tag using the exopeptidase carboxypeptidase A (CPA). CPA removes amino acids from the carboxyl terminus of proteins, however, it is unable to cleave arginine, lysine, or proline. There is an arginine at the second to last position of the native HCII. Therefore, we assumed a CPA digest would remove the hexahistidine tag and the final serine residue of HCII stopping at the penultimate arginine. In the top panel of FIG. 3, we see that a rHCII-CHis$_6$ pre-CPA digest shows an increased rate of thrombin inhibition and a shift to a lower heparin requirement. When digested with CPA, the curve of thrombin inhibition shifts to lower rates of inhibition and the required heparin concentration increases. In contrast, the curves of thrombin inhibition by wt-rHCII do not drastically change before or after the CPA digest (FIG. 3, middle panel). Control experiments with EDTA added to rHCII-CHis$_6$ prior to the exopeptidase verified that the loss of rHCII-CHis$_6$ activity was due to the effect of active CPA.

EXAMPLE 12 rHCII-CHis$_5$Pro Mutant

To confirm that the function of CPA in reversing the enhanced activity was on the hexahistidine portion of the protein, we expressed a mutant that had a His$_5$Pro carboxyl-terminal tag (FIG. 4; SEQ ID NO:6 and SEQ ID NO:7). This mutant, rHCII-CHis$_5$Pro, inhibits thrombin in the absence of glycosaminoglycans ($3.2 \times 10^4$ M$^{-1}$ min$^{-1}$) at rates ~2-fold higher than wt-rHCII, and has increased heparin cofactor activity at a lower maximal heparin concentration ($1.87 \pm 0.37 \times 10^9$ M$^{-1}$ min$^{-1}$ at 10 $\mu$g/mL heparin; data not included). We hypothesized that this mutant should be resistant to CPA digestion because of the carboxyl terminal proline residue. Pre-digested rHCII-CHis$_5$Pro has similar properties to that of rHCII-CHis$_6$ with an increased inhibition rate and a lower heparin requirement; however, as expected, its activity does not change appreciably after treatment with CPA (bottom panel, FIG. 3).

Thus, the disclosed HCII mutants containing carboxyl terminal extensions can be designed so as to give "short-acting" (e.g., rHCII-CHis$_6$) and "long-acting" (e.g., rHCII-CHis$_5$Pro) anti-thrombin compositions. Carboxypeptidase is found in the systemic circulation, and may remove the carboxyl terminal extension from the mutant HCII proteins, thereby reversing the enhancing effect of this mutation. In mutants in which the carboxyl-terminal amino acid is proline or is otherwise blocked, carboxypeptidase cannot cleave the carboxyl-most peptide bond. Such carboxyl-terminal blocked HCII mutants will therefore have "long-acting" HCII effects in vitro and in vivo.

EXAMPLE 13

Thrombin Inhibition by P1 Loop - CHis$_6$ Mutant

Since we have found that rHCII-CHis$_6$ inhibits thrombin at rates comparable to ATIII, we investigated whether we could further increase its activity. Previously, Tollefsen and colleagues (Derechin, V. M., Blinder, M. A., and Tollefsen, D. M. (1990) *J. Biol. Chem.* 265(10), 5623–5628; Han, J. H., Van Deerlin, V. M. D., and Tollefsen, D. M. (1997) *J. Biol. Chem.* 272, 8243–8249) and our laboratory (Ciaccia, A. V., Willemze, A. J., and Church, F. C. (1997) *J. Biol. Chem.* 272(2), 888–893) showed that a mutation at the reactive site residue PI (L444R), increases the rate of thrombin inhibition in the absence of glycosaminoglycan by almost 2 orders of magnitude compared to wt-rHCII. Therefore, we expressed an HCII mutant that contained both L444R and a hexahistidine carboxyl tag. In the absence of glycosaminoglycan, the rate of thrombin inhibition by rHCII-L444R-CHis$_6$ ($1.59 \pm 0.26 \times 10^6$ M$^{-1}$ min$^{-1}$) was ~100-fold greater than rHCII-CHis$_6$, but it was not significantly different than that of rHCII-L444R ($1.3 \pm 0.30 \times 10^6$ M$^{-1}$ min$^{-1}$; Kunkel, T. A., Roberts, J. D., and Zakour, R. A. (1987) *Meth. Enzymol.* 154, 367–382). This indicates that without glycosaminoglycan, addition of the histidine tag to the reactive site mutation in HCII does not increase activity compared to rHCII-L444R alone.

In the presence of glycosaminoglycan, heparin accelerated rHCII-L444R-CHis$_6$ to a greater extent than rHCII-L444R (rHCII-L444R-CHis$_6$ is $2.47 \pm 0.35 \times 10^8$ M$^{-1}$ min$^{-1}$ and rHCII-L444R is $1.93 \pm 0.38 \times 10^8$ M$^{-1}$ min$^{-1}$). Similar results were obtained with dermatan sulfate (rHCII-L444R-CHis$_6$ is $8.81 \pm 0.20 \times 10^8$ M$^{-1}$ min$^{-1}$ and rHCII-L444R is $2.84 \pm 0.24 \times 10^6$ M$^{-1}$ min$^{-1}$; Kunkel, T. A., Roberts, J. D., and Zakour, R. A. (1987) *Meth. Enzymol.* 154, 367–382).

However, with glycosaminoglycans the rates of the L444R-containing rHCII mutants are significantly lower than both wt-rHCII and rHCII-CHis$_6$ (see Table II). Addition of the carboxyl-terminal tag to rHCII-L444R decreases both the heparin (~20 $\mu$g/mL) and dermatan sulfate (~200 $\mu$g/mL) concentration at which these maximal rates occur (glycosaminoglycan-dependent curves for rHCII-L444R and rHCII-L444R-CHis$_6$ are both broad and flat in shape, see Kunkel, T. A., Roberts, J. D., and Zakour, R. A. (1987) *Meth. Enzymol.* 154, 367–382; Tollefsen, D. M., and Pestka, C. A. (1985) *Blood* 66(4), 769–774; Griffith, M. J., Carraway, T., White, G. C., and Dombrose, F. A. (1983) *Blood* 61(1), 111–118). Recombinant HCII-L444R-CHis$_6$ eluted off heparin-Sepharose at 600 mM NaCl while rHCII-L444R (350 mM NaCl) was the same as wt-rHCII. These data further suggests that the histidine tag contributes to enhanced heparin binding activity.

EXAMPLE 14

Effect of Hirugen on Inhibition of Thrombin in the Absence of Glycosaminoglycan

Figure 5:
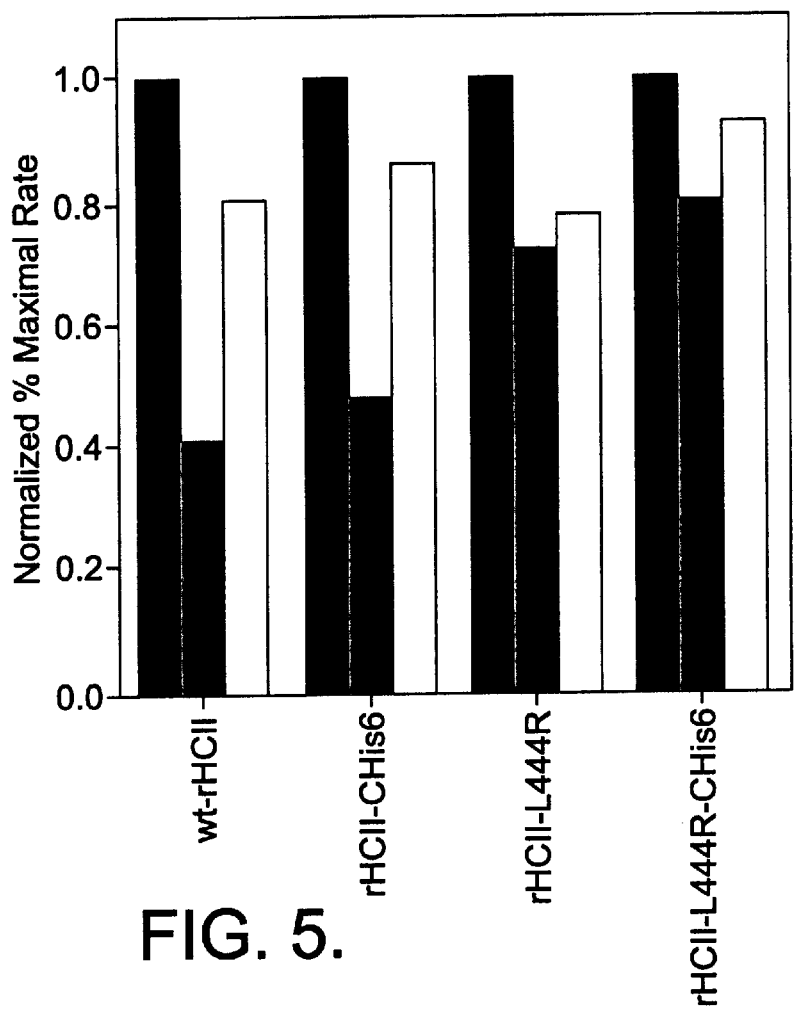
FIG. 5 demonstrates the effect of hirugen on the rate of thrombin inhibition by wt-rHCII and rHCII-CHis$_6$ mutants. The various rHCIIs were incubated with α-thrombin in the absence of hirugen (■), in the presence of hirugen (▨) or in the presence of control peptide ❏, and the residual thrombin activity was determined. The data are presented as normalized % maximal rate of inhibition using the following rate constants of inhibition ($k_2$) in the absence of peptide: wt-rHCII is $1.52 \times 10^4$ M$^{-1}$ min$^{-1}$; rHCII-CHis$_6$ is $1.86 \times 10^4$ M$^{-1}$ min$^{-1}$; rHCII-L444R is $1.87 \times 10^6$ M$^{-1}$ min$^{-1}$; and rHCII-L444R-CHis$_6$ is $2.12 \times 10^6$ M$^{-1}$ min$^{-1}$. The above data represent the means of two determinations in triplicate.

Thrombin inhibition in the presence of hirugen was performed to examine the potential role of thrombin anion-binding exosite-1 in the enhanced activity of the rHCII-CHis$_6$ mutants (with and without L444R). Hirugen interferes with the HCII-thrombin inhibition reaction by binding to anion-binding exosite-1. Hirugen has a similar effect on the progressive antithrombin activity of rHCII-CHis$_6$ and wt-rHCII, with rates being reduced >50% (FIG. 5). There is less of an effect of hirugen to modulate thrombin inhibition by rHCII-L444R-CHis$_6$ and rHCII-L444R (FIG. 5). The effect of hirugen is specific since a control peptide that is highly negatively charged did not significantly block (changes were from ~10–20% in the absence of added peptide) the HCII-thrombin reactions (FIG. 5). These data imply that the hexahistidine tag does not alter the manner in which HCII interacts with anion-binding exosite-1 of thrombin in the presence of hirugen.

EXAMPLE 15

The Effect of pH on the Rate of Thrombin Inhibition by rHCII-CHis$_6$

Figure 6:
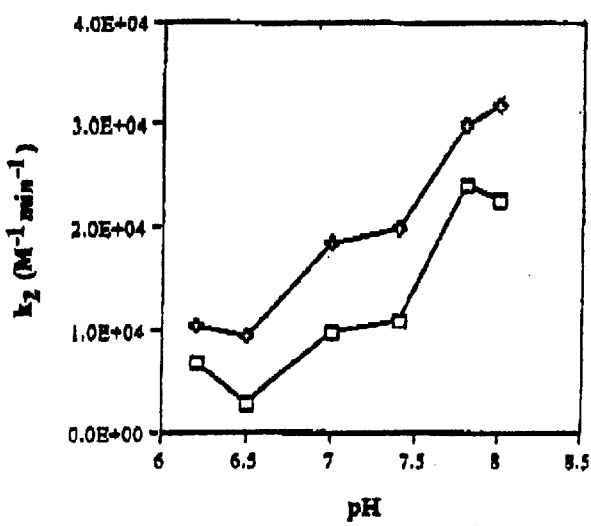
FIG. 6 shows the pH titration curves for inhibition of thrombin by wt-rHCII ❏ and rHCII-CHis$_6$ (+).

Histidine residues have a pKa of 6.5. Therefore, it is possible that the enhanced thrombin inhibitory activity of rHCII-CHis$_6$ (assayed at pH 7.4) is attributable to a charge on the carboxyl terminal tag. An assay was designed to measure thrombin inhibition by rHCII-CHis$_6$ and wt-rHCII from pH 6.2 to pH 8. FIG. 6 shows the pH titration curves for inhibition of thrombin by rHCII-CHis$_6$ and wt-rHCII. It can be seen that although the inhibition by rHCII-CHis$_6$ is greater than that by wt-rHCII, the two curves follow the same shape indicating that both inhibitors are affected by the change in pH in the same way. The histidine tag on rHCII-CHis$_6$ does not seem to affect the shape of the curve from below the pKa of the histidine residues (pH 6.2), where the residues should be charged, up to pH 8, where the residues should not be charged. The results do suggest that the two curves may diverge above pH 8.

EXAMPLE 16

Carboxyl-Terminal Histidine-Tagged rATIII

To examine whether augmentation of activity was a general phenomenon of other glycosaminoglycan binding serpins, we added a hexahistidine carboxyl tag to recombinant wild-type ATIII. Again we used Kunkel's method to insert six histidine codons directly before the TAA stop codon. We used a baculoviral expression system and 60–150 $\mu$g of protein was obtained from four T150 flasks of High- Five™ cells infected with recombinant viral stock. Immunoblot analysis showed that purified rATIII-CHis$_6$ co-migrated with wt-rATIII as a single band.

In the absence of glycosaminoglycan we compared the rates of thrombin, Factor Xa and trypsin inhibition (summarized in Table I). As a control to evaluate recombinant ATIII proteins, we obtained inhibition rates of $1.32\pm0.22\times10^5$ M$^{-1}$ min$^{-1}$ and $9.15\pm0.44\times10^4$ M$^{-1}$ min$^{-1}$ for thrombin and Factor Xa with human plasma-derived ATIII, respectively. The rates of thrombin and trypsin inhibition by rATIII-CHis$_6$ are essentially unchanged as compared to wt-rATIII. However, the rate of Factor Xa inhibition by rATIII-CHis$_6$ is $9.87\pm0.57\times10^4$ M$^{-1}$ min$^{-1}$, which is significantly lower than wt-rATIII ($1.64\pm0.12\times10^5$ M$^{-1}$ min$^{-1}$).

Figure 7A:
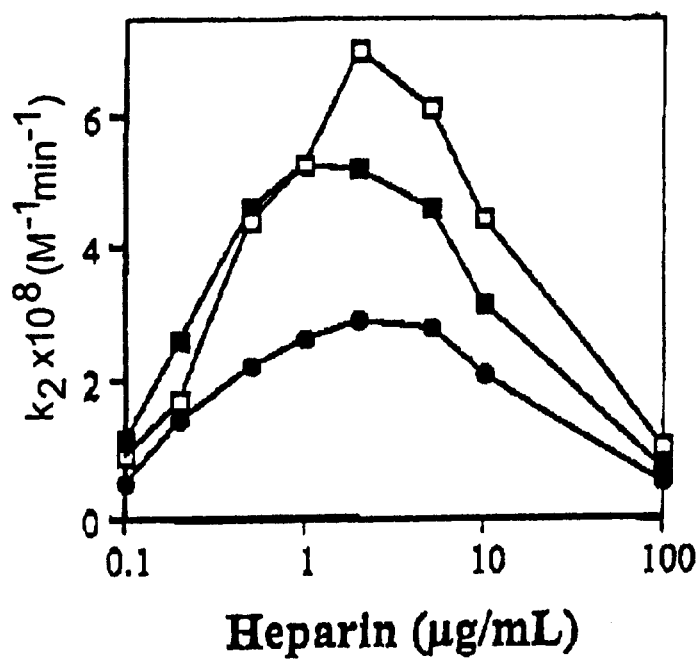
FIG. 7 is a graphical representation of the inhibition of thrombin and Factor Xa by rATIII mutants in the presence of heparin. Thrombin or Factor Xa assays in the presence of heparin were performed with plasma purified α-thrombin (top panel) or actor Xa (bottom panel) and increasing amounts of heparin comparing plasma purified ATIII (❏) wt-rATIII (■) and rATIII-CHis$_6$ (●). The curves are the averages of two or three protein preps assayed two to three times each.
Figure 7B:
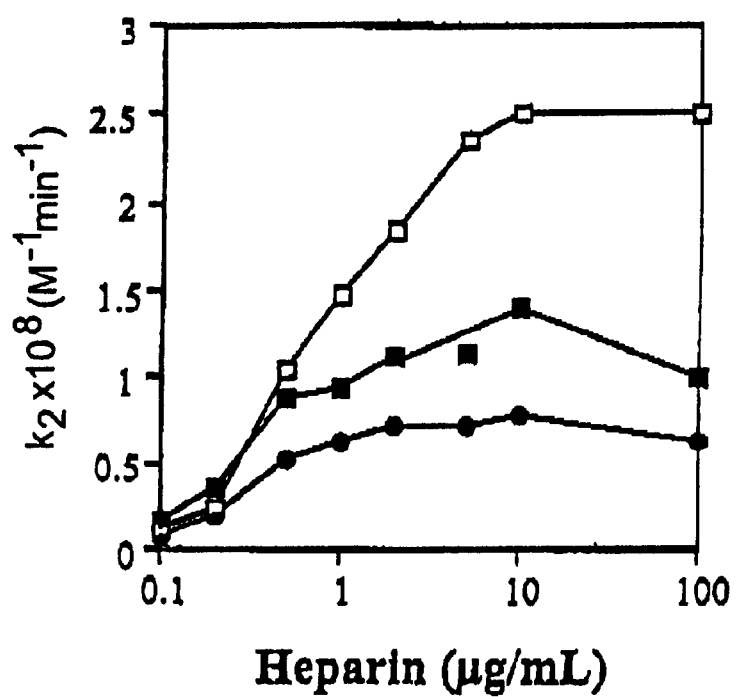

FIG. 7 shows the heparin-catalyzed ATIII inhibition of thrombin (top panel) and Factor Xa (bottom panel). We see that there is an almost two-fold slower rate of thrombin inhibition by rATIII-CHis$_6$ ($2.87\pm0.54\times10^8$ M$^{-1}$ min$^{-1}$) as compared to wt-rATIII ($5.26\pm0.68\times10^8$ M$^{-1}$ min$^{-1}$). The rates of Factor Xa inhibition in the presence of heparin show the same trend. Proteolysis of rATIII-CHis$_6$ with CPA should, theoretically, remove the entire histidine tag leaving the intact native protein since the final amino acid of ATIII is lysine. Rates of thrombin inhibition by rATIII-CHis$_6$ with 10 μg/mL heparin increased 40% after treatment with CPA, compared to wt-rATIII (data not shown). To compare the recombinant ATIII proteins to plasma-derived ATIII with heparin, we obtained maximal rates of inhibition of $6.94\pm0.25\times10^8$ M$^{-1}$ min$^{-1}$ and $2.51\pm0.083\times10^8$ M$^{-1}$ min$^{-1}$, for thrombin and Factor Xa, respectively (FIG. 7). The curves in FIG. 7 illustrate that the amount of heparin required for maximal inhibition of either thrombin or Factor Xa by these ATIII derivatives does not change significantly when the histidine tag is added. The data are summarized in Table II.

We then assessed the ability of the rATIII molecules to bind heparin-Sepharose. As shown in Table II, rATIII-CHis$_6$ eluted at the same NaCl concentration as wt-rATIII (975 mM). These data support the previous data showing no shift in the amount of heparin required for antithrombin or anti-Factor Xa activity.

EXAMPLE 17

Histidine-Tagged rHCII in Plasma-Based Thrombin Inhibition Assays

The data that has been presented to this point indicates that rHCII-CHis$_6$ is an excellent thrombin inhibitor and is now comparable to the physiologic inhibitor ATIII in its rates and heparin requirements. The next set of experiments was performed to assess the potential of rHCII-CHis$_6$ as a therapeutic agent in a more complex setting (e.g., plasma).

The results comparing rHCII-CHis$_6$ to wt-rHCII are summarized in Table III. At each plasma condition the rates of thrombin inhibition was measured in the presence of 1 μg/mL of heparin. The thrombin inhibitory capabilities of rHCII-CHis$_6$ with each plasma condition are significantly greater than those of wt-rHCII performed using the same conditions. Thrombin inhibition in REF plasma, which would contain both HCII and ATIII, gave thrombin inhibition rates that are increased 1.5-fold for rHCII-CHis$_6$ compared to wt-rHCII. Using DEF plasma, which is totally deficient in ATIII, the enhancement of thrombin inhibition by rHCII-CHis$_6$ over wt-rHCII was more apparent with a 4.6-fold increased rate. In a 50:50 mixture of REF/DEF, which mimics a heterozygous ATIII deficiency, rHCII-CHis$_6$ inhibition of thrombin was increased 1.5-fold compared to wt-rHCII. Furthermore, the rates of inhibition in the presence of 50 μg/mL of dermatan sulfate are also significantly greater with rHCII-CHis$_6$ than with wt-rHCII for each of the plasma conditions tested, with rates increased about 1.2–1.3-fold (Table III). These data suggest that rHCII-CHis$_6$ is a significantly better thrombin inhibitor than is wt-rHCII in the presence of glycosaminoglycans in a more complex assay setting.

Although the foregoing invention has been described in some detail by way of illustration and example for purposes of clarity and understanding, it will be obvious that certain changes and modifications may be practiced within the scope of the appended claims.

TABLE III

Inhibition of Thrombin Activity in Plasma[a]

| | Inhibition Rate[b] $k_2 \times 10^8$ (M$^{-1}$min$^{-1}$) | | | |
|---|---|---|---|---|
| | Heparin (1 μg/mL) | | Dermatan Sulfate (50 μg/mL) | |
| Plasma Addition | wt-rHCII | rHCII-CHis$_6$ | wt-rHCII | rHCII-CHis$_6$ |
| Normal Reference (REF) | 22 ± .17 | 3.3 ± .37[c] | 5.7 ± .45 | 7.2 ± .55[d] |
| ATIII Deficient (DEF) | .26 ± .050 | 1.2 ± .10[c] | 6.5 ± .50 | 7.5 ± .59[d] |
| 50:50 Mixture (REF/DEF) | 1.9 ± .050 | 2.8 ± .18[c] | 5.8 ± .24 | 7.0 ± .48[d] |

[a]Inhibition of thrombin activity (1 nM) in the presence of wt-rHCII and rHCII-CHis$_6$ (10 nM) and glycosaminoglycan in normal human reference plasma (REF), Antithrombin III deficient human plasma (DEF) or a 50:50 mixture of these plasmas (REF/DEF).
Inhibition rates are given as the average inhibition rate ± S.D. The statistical significance of the data was evaluated using Student's t-tests; P-values <0.05 were considered significant.
[b]Rate constants are the mean values of 3–6 determinations with 3 different preparations of recombinant proteins.
[c]p≦0.001 compared with wt-rHCII.
[d]p≦0.01 compared with wt-rHCII.

That which is claimed is:

1. An isolated DNA encoding a mutant heparin cofactor II comprising, in combination, a heparin cofactor II and a carboxyl terminal amino acid extension, wherein said carboxyl terminal amino acid extension comprises a histidine residue and confers enhanced anti-thrombin activity to said mutant heparin cofactor II.

2. The isolated DNA of claim 1, wherein said amino acid extension is from 2 to 12 amino acids in length.

3. The isolated DNA of claim 1, wherein said amino acid extension is from 5 to 8 amino acids in length.

4. The isolated DNA of claim 1, wherein said mutant heparin cofactor II is a human mutant heparin cofactor II.

5. The isolated DNA of claim 1, wherein said amino acid extension comprises at least 30% histidine residues.

6. The isolated DNA of claim 1, wherein said amino acid extension comprises at least 4 histidine residues.

7. The isolated DNA of claim 1, wherein said amino acid extension further comprises a carboxyl terminal proline residue.

8. A vector comprising the isolated DNA of claim 1.

9. The vector according to claim 8, wherein said vector is selected from the group consisting of a bacteriophage, plasmid, YAC, baculovirus, and animal virus.

10. A cell containing the vector of claim 8.

11. The cell according to claim 10, wherein said cell is a mammalian cell.

12. The cell according to claim 10, wherein said cell is an insect cell.

13. The cell according to claim 10, wherein said cell is selected from the group consisting of a stably-transformed cattle, sheep, goat, and pig cell.

14. The isolated DNA of claim 1 selected from the group consisting of:

(a) DNA having the sequence of SEQ ID NO:4; and (b) DNA that hybridizes to the DNA of SEQ ID NO:4 under stringent conditions, defined by a wash stringency of 0.3 M NaCl, 0.03 M sodium citrate, 0.1% SDS at 60° C., and encodes a mutant heparin cofactor 11 molecule comprising a carboxyl terminal amino acid extension, wherein said carboxyl terminal amino acid extension comprises a histidine residue and confers enhanced anti-thrombin activity to said mutant heparin cofactor II.

15. A vector comprising the isolated DNA of claim 14.

16. The vector according to claim 15, wherein said vector is selected from the group consisting of a bacteriophage, plasmid, YAC, baculovirus, and animal virus.

17. A cell containing the vector of claim 15.

18. The cell according to claim 17, wherein said cell is a mammalian cell.

19. The cell according to claim 17, wherein said cell is an insect cell.

20. The cell according to claim 17, wherein said cell is selected from the group consisting of a stably-transformed cattle, sheep, goat, and pig cell.

21. The isolated DNA of claim 1 selected from the group consisting of:
(a) DNA having the sequence of SEQ ID NO:6; and
(b) DNA that hybridizes to the DNA of SEQ ID NO:6 under stringent conditions, defined by a wash stringency of 0.3 M NaCl, 0.03 M sodium citrate, 0.1% SDS at 60° C., and encodes a mutant heparin cofactor II molecule comprising a carboxyl terminal amino acid extension, wherein said carboxyl terminal amino acid extension comprises a histidine residue and confers enhanced anti-thrombin activity to said mutant heparin cofactor II.

22. A vector comprising the isolated DNA of claim 21.

23. The vector according to claim 22, wherein said vector is selected from the group consisting of a bacteriophage, plasmid, YAC, baculovirus, and animal virus.

24. A cell containing the vector of claim 23.

25. The cell according to claim 24, wherein said cell is a mammalian cell.

26. The cell according to claim 24, wherein said cell is an insect cell.

27. The cell according to claim 24, wherein said cell is selected from the group consisting of a stably-transformed cattle, sheep, goat, and pig cell.

28. A method of producing a mutant heparin cofactor II having enhanced anti-thrombin activity comprising expressing the isolated DNA of claim 1 in a host cell.

29. The method of claim 28, wherein the host cell is selected from the group consisting of a bacterial, yeast, insect, and mammalian cell.

30. The cell according to claim 28, wherein said cell is selected from the group consisting of a stably-transformed cattle, sheep, goat, and pig cell.

31. The method of claim 28, wherein the isolated DNA is encoded by a vector selected from the group consisting of a bacteriophage, plasmid, YAC, baculovirus, and animal virus.

32. The method of claim 28, wherein the isolated DNA is expressed in a mammalian tissue culture system.

33. The method according to claim 28, wherein the isolated DNA is expressed by a transgenic animal.

34. An isolated DNA encoding a mutant heparin cofactor II comprising, in combination, a heparin cofactor II and a carboxyl terminal amino acid extension, wherein said carboxyl terminal amino acid extension consists of histidine residues and confers enhanced anti-thrombin activity to said mutant heparin cofactor II.

35. The isolated DNA of claim 34, wherein said carboxyl terminal extension consists of from 2 to 20 residues.

36. The isolated DNA of claim 35, wherein said carboxyl terminal extension consists of 5 or 6 residues.

37. The isolated DNA of claim having the sequence given as SEQ ID NO:4.

38. An isolated DNA encoding a mutant heparin cofactor II comprising, in combination, a heparin cofactor II and a carboxyl terminal amino acid extension, wherein said carboxyl terminal amino acid extension consists of histidine residues and a carboxyl terminal proline residue and confers enhanced anti-thrombin activity to said mutant heparin cofactor II.

39. The isolated DNA of claim 38, wherein said carboxyl terminal extension consists of from 2 to 20 residues.

40. The isolated DNA of claim 39, wherein said carboxyl terminal extension consists of 5 histidine residues and a carboxyl terminal proline.

41. The isolated DNA of claim 40 having the sequence given as SEQ ID NO:6.

* * * * *

UNITED STATES PATENT AND TRADEMARK OFFICE
CERTIFICATE OF CORRECTION

PATENT NO. : 6,207,419 B1
DATED : March 27, 2001
INVENTOR(S) : Church et al.

It is certified that error appears in the above-identified patent and that said Letters Patent is hereby corrected as shown below:

Title page,
Item [56], References Cited, OTHER PUBLICATIONS, should read -- Bauman et al.; "Serpendipity": Enhanced Antithrombotic Activity of a Novel Recombinant Heparin Cofactor II, Blood, 92: 10 Part 2 of 2, 1998. --
should read -- Tewari et al.; Yama/CPP32β, a Mammalian Homolog of CED-3, is a CrmA-Inhibitable Protease that Cleaves the Death Substrate Poly(ADP-Ribose) Polymerase; Cell, 81:801-809 June 2, 1995. --

Column 36,
Line 19, after "of claim" please insert -- 36. --

Signed and Sealed this

Twenty-eighth Day of June, 2005

JON W. DUDAS
*Director of the United States Patent and Trademark Office*